(12) United States Patent
Terao et al.

(10) Patent No.: US 11,542,301 B2
(45) Date of Patent: Jan. 3, 2023

(54) FC-BINDING PROTEIN HAVING IMPROVED ANTIBODY SEPARATION ABILITY, AND METHOD FOR SEPARATING ANTIBODY USING SAME

(71) Applicant: TOSOH CORPORATION, Yamaguchi (JP)

(72) Inventors: Yosuke Terao, Kanagawa (JP); Yoshiharu Asaoka, Kanagawa (JP); Ryoko Otake, Kanagawa (JP); Satoshi Endo, Kanagawa (JP); Naoki Yamanaka, Kanagawa (JP); Yukie Yamamoto, Kanagawa (JP); Seigo Oe, Kanagawa (JP)

(73) Assignee: TOSOH CORPORATION, Yamaguchi (JP)

( * ) Notice: Subject to any disclaimer, the term of this patent is extended or adjusted under 35 U.S.C. 154(b) by 660 days.

(21) Appl. No.: 16/486,380

(22) PCT Filed: Feb. 7, 2018

(86) PCT No.: PCT/JP2018/004202
§ 371 (c)(1),
(2) Date: Aug. 15, 2019

(87) PCT Pub. No.: WO2018/150973
PCT Pub. Date: Aug. 23, 2018

(65) Prior Publication Data
US 2020/0223885 A1 Jul. 16, 2020

(30) Foreign Application Priority Data

Feb. 20, 2017 (JP) .............................. JP2017-028974
Apr. 4, 2017 (JP) .............................. JP2017-074727
Jun. 2, 2017 (JP) .............................. JP2017-109681

(51) Int. Cl.
*C07K 1/22* (2006.01)
*C07K 17/00* (2006.01)
*C07K 14/00* (2006.01)
*C07K 16/00* (2006.01)

(52) U.S. Cl.
CPC ................ *C07K 1/22* (2013.01); *C07K 14/00* (2013.01); *C07K 16/00* (2013.01)

(58) Field of Classification Search
CPC ....... C07K 1/22; C07K 2317/52; C07K 17/00
USPC ...................................................... 424/133.1
See application file for complete search history.

(56) References Cited

U.S. PATENT DOCUMENTS

| | | | | |
|---|---|---|---|---|
| 10,221,210 B2 * | 3/2019 | Bolton | .................. | C12P 21/005 |
| 10,815,289 B2 * | 10/2020 | Asaoka | ................ | C07K 16/065 |
| 2013/0084648 A1 * | 4/2013 | Bolton | ...................... | C07K 1/22 530/391.1 |
| 2016/0222081 A1 | 8/2016 | Asaoka et al. | | |
| 2017/0218044 A1 | 8/2017 | Asaoka et al. | | |
| 2021/0116445 A1 * | 4/2021 | Terao | ................... | G01N 33/543 |
| 2021/0261605 A1 * | 8/2021 | Watanabe | ................ | C07K 1/22 |

FOREIGN PATENT DOCUMENTS

| | | |
|---|---|---|
| EP | 3702462 A1 | 9/2020 |
| JP | 2014-527518 | 10/2014 |
| JP | 2015-019615 | 2/2015 |
| JP | 2015-083558 | 4/2015 |
| JP | 2015-086216 | 5/2015 |
| JP | 2017/118871 | 7/2017 |
| WO | 2013/013193 A1 | 1/2013 |
| WO | 2015/199154 | 12/2015 |
| WO | 2019/083048 A1 | 5/2019 |

OTHER PUBLICATIONS

Kiyoshi et al. (Science Reports, 8(1):3955—(Mar. 2, 2018)).*
Kosuge et al (Biotechnol Prog Nov.-Dec. 2020; 36(6): e3016).*
Freimoser-Grundschober et al (Journal of Chromatography, 1610:1-9 (2020)).*
P. Bruhn et al., "Blood, 16", 2009, pp. 3716-3725.
P. Sonderman et al., "Nature, 406", 2000, pp. 267-2735.
International Search Report issued in International Patent Application No. PCT/JP2018/004202, dated May 1, 2018 with English translation.
International Preliminary Report on Patentability issued in International Patent Application No. PCT/JP2018/004202, dated Aug. 20, 2019 with English translation.

* cited by examiner

*Primary Examiner* — Lynn A Bristol
(74) *Attorney, Agent, or Firm* — Greenblum & Bernstein, P.L.C.

(57) ABSTRACT

The present application addresses the problem of providing an Fc-binding protein having an improved antibody separation ability. The present application also addresses the problem of providing a high-accuracy antibody separation method using an insoluble carrier having the protein immobilized thereon. The problems can be solved by: an Fc-binding protein in which at least an amino acid substitution at a specific position therein occurs and which has reduced affinity for an antibody; and an antibody separation method including allowing an equilibration buffer solution to pass through a column in which an insoluble carrier having the protein immobilized thereon is filled to equilibrate the column, adding a solution containing an antibody to cause the adsorption of the antibody onto the carrier, and eluting the antibody adsorbed on the carrier using an elution solution.

7 Claims, 8 Drawing Sheets
Specification includes a Sequence Listing.

FIG. 1
| 1 | 16 | 17 | 208 | 209 | 229 | 230 | 254 |
| S | | EC | | TM | | C | |
FIG. 2
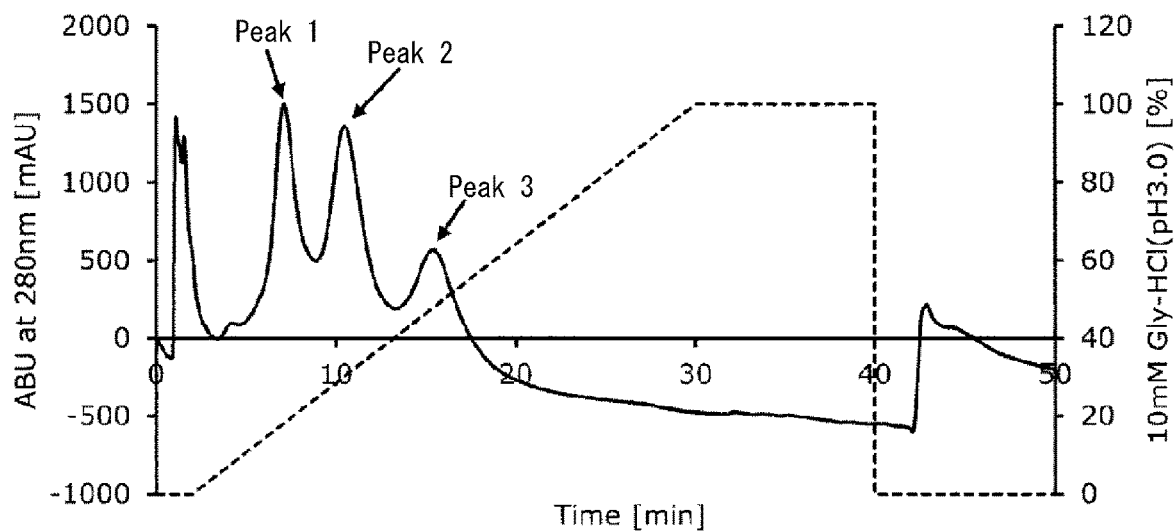
FIG. 3
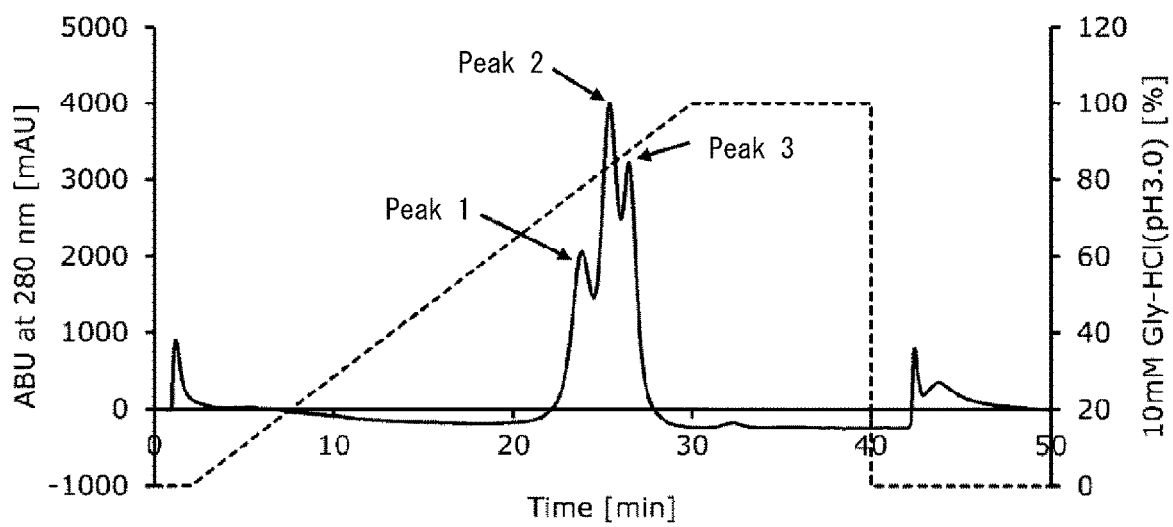

```
                         SEQUENCE LISTING

<160> NUMBER OF SEQ ID NOS: 42

<210> SEQ ID NO 1
<211> LENGTH: 254
<212> TYPE: PRT
<213> ORGANISM: Homo sapiens

<400> SEQUENCE: 1

Met Trp Gln Leu Leu Leu Pro Thr Ala Leu Leu Leu Val Ser Ala
1               5                   10                  15

Gly Met Arg Thr Glu Asp Leu Pro Lys Ala Val Val Phe Leu Glu Pro
            20                  25                  30

Gln Trp Tyr Arg Val Leu Glu Lys Asp Ser Val Thr Leu Lys Cys Gln
        35                  40                  45

Gly Ala Tyr Ser Pro Glu Asp Asn Ser Thr Gln Trp Phe His Asn Glu
    50                  55                  60

Ser Leu Ile Ser Ser Gln Ala Ser Ser Tyr Phe Ile Asp Ala Ala Thr
65                  70                  75                  80

Val Asp Asp Ser Gly Glu Tyr Arg Cys Gln Thr Asn Leu Ser Thr Leu
                85                  90                  95

Ser Asp Pro Val Gln Leu Glu Val His Ile Gly Trp Leu Leu Leu Gln
            100                 105                 110

Ala Pro Arg Trp Val Phe Lys Glu Glu Asp Pro Ile His Leu Arg Cys
        115                 120                 125

His Ser Trp Lys Asn Thr Ala Leu His Lys Val Thr Tyr Leu Gln Asn
    130                 135                 140

Gly Lys Gly Arg Lys Tyr Phe His His Asn Ser Asp Phe Tyr Ile Pro
145                 150                 155                 160

Lys Ala Thr Leu Lys Asp Ser Gly Ser Tyr Phe Cys Arg Gly Leu Val
                165                 170                 175

Gly Ser Lys Asn Val Ser Ser Glu Thr Val Asn Ile Thr Ile Thr Gln
            180                 185                 190

Gly Leu Ala Val Ser Thr Ile Ser Ser Phe Phe Pro Pro Gly Tyr Gln
        195                 200                 205

Val Ser Phe Cys Leu Val Met Val Leu Leu Phe Ala Val Asp Thr Gly
    210                 215                 220

Leu Tyr Phe Ser Val Lys Thr Asn Ile Arg Ser Ser Thr Arg Asp Trp
225                 230                 235                 240

Lys Asp His Lys Phe Lys Trp Arg Lys Asp Pro Gln Asp Lys
                245                 250

<210> SEQ ID NO 2
<211> LENGTH: 20
<212> TYPE: DNA
<213> ORGANISM: Artificial Sequence
<220> FEATURE:
<223> OTHER INFORMATION: Oligonucleotide

<400> SEQUENCE: 2
taatacgact cactataggg                                               20

<210> SEQ ID NO 3
<211> LENGTH: 19
<212> TYPE: DNA
```

<213> ORGANISM: Artificial Sequence
<220> FEATURE:
<223> OTHER INFORMATION: Oligonucleotide

<400> SEQUENCE: 3
tatgctagtt attgctcag                                                        19

<210> SEQ ID NO 4
<211> LENGTH: 216
<212> TYPE: PRT
<213> ORGANISM: Artificial Sequence
<220> FEATURE:
<223> OTHER INFORMATION: MalE-CD16a-6His

<400> SEQUENCE: 4

```
Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Ala Met
                20                  25                  30

Gly Met Arg Thr Glu Asp Leu Pro Lys Ala Val Val Phe Leu Glu Pro
            35                  40                  45

Gln Trp Tyr Arg Val Leu Glu Lys Asp Ser Val Thr Leu Lys Cys Gln
        50                  55                  60

Gly Ala Tyr Ser Pro Glu Asp Asn Ser Thr Gln Trp Phe His Asn Glu
65                  70                  75                  80

Ser Leu Ile Ser Ser Gln Ala Ser Ser Tyr Phe Ile Asp Ala Ala Thr
                85                  90                  95

Val Asp Asp Ser Gly Glu Tyr Arg Cys Gln Thr Asn Leu Ser Thr Leu
            100                 105                 110

Ser Asp Pro Val Gln Leu Glu Val His Ile Gly Trp Leu Leu Leu Gln
        115                 120                 125

Ala Pro Arg Trp Val Phe Lys Glu Glu Asp Pro Ile His Leu Arg Cys
    130                 135                 140

His Ser Trp Lys Asn Thr Ala Leu His Lys Val Thr Tyr Leu Gln Asn
145                 150                 155                 160

Gly Lys Gly Arg Lys Tyr Phe His His Asn Ser Asp Phe Tyr Ile Pro
                165                 170                 175

Lys Ala Thr Leu Lys Asp Ser Gly Ser Tyr Phe Cys Arg Gly Leu Val
            180                 185                 190

Gly Ser Lys Asn Val Ser Ser Glu Thr Val Asn Ile Thr Ile Thr Gln
        195                 200                 205

Gly Gly His His His His His His
    210                 215
```

<210> SEQ ID NO 5
<211> LENGTH: 216
<212> TYPE: PRT
<213> ORGANISM: Artificial Sequence
<220> FEATURE:
<223> OTHER INFORMATION: FcR9

<400> SEQUENCE: 5

```
Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Ala Met
                20                  25                  30

Gly Met Arg Thr Glu Asp Leu Pro Lys Ala Glu Val Ile Leu Glu Pro
            35                  40                  45
```

```
Gln Trp Asn Arg Val Leu Glu Lys Asp Ser Val Thr Leu Lys Cys Arg
 50                  55                  60
Gly Ala Tyr Ser Pro Glu Asp Asn Ser Thr Gln Trp Phe His Asn Glu
 65                  70                  75                  80
Ser Leu Ile Ser Ser Gln Ala Ser Ser Tyr Leu Ile Asp Ala Ala Thr
                 85                  90                  95
Val Asp Asp Ser Gly Glu Tyr Arg Cys Gln Thr Ser Leu Ser Thr Leu
            100                 105                 110
Ser Asp Pro Val Gln Leu Glu Val His Ile Gly Trp Leu Leu Leu Gln
            115                 120                 125
Ala Pro Arg Trp Glu Phe Lys Glu Gly Asp Pro Ile His Leu Arg Cys
130                 135                 140
His Ser Trp Lys Asn Thr Ala Leu His Lys Val Thr Tyr Leu Gln Asn
145                 150                 155                 160
Gly Lys Gly Arg Lys Tyr Phe His His Asn Ser Asp Phe Tyr Ile Pro
                165                 170                 175
Lys Ala Thr Leu Lys Asp Ser Gly Ser Tyr Ser Cys Arg Gly Leu Val
            180                 185                 190
Gly Ser Lys Asn Val Ser Ser Glu Thr Val Asn Ile Thr Ile Thr Gln
            195                 200                 205
Gly Gly His His His His His His
210                 215
```

<210> SEQ ID NO 6
<211> LENGTH: 648
<212> TYPE: DNA
<213> ORGANISM: Artificial Sequence
<220> FEATURE:
<223> OTHER INFORMATION: Polynucleotide encoding FcR9

<400> SEQUENCE: 6

```
atgaaaataa aaacaggtgc acgcatcctc gcattatccg cattaacgac gatgatgttt      60
tccgcctcgg ctctcgccaa aatcgaagaa gccatgggca tgcgtaccga agatctgccg     120
aaagcggagg tgattctgga accgcagtgg aatcgcgtgc tggagaaaga ttctgtgacc     180
cttaaatgcc ggggcgcgta tagcccggaa gataacagca cccagtggtt ccacaatgaa     240
agcctgattt ccagccaggc gagcagctac cttattgatg cggcgacggt ggatgatagc     300
ggcgaatatc gttgccagac cagcctgagc accctgagcg atccggtgca gctggaggtg     360
cacatcgggt ggcttctgtt acaggctcca cggtgggagt tcaaagaggg ggatccgatt     420
catctgcggt gtcactcctg gaagaatacc gccctgcata agtgacccta cctgcaaaac     480
ggcaagggcc gcaagtattt ccaccacaac tccgacttct atattcccaa agcgacgctg     540
aaggacagcg gcagctattc ctgccgtggg ctggtgggca gcaaaaatgt gagcagcgag     600
accgtgaata ttaccattac ccaagggggc catcatcatc atcatcat               648
```

<210> SEQ ID NO 7
<211> LENGTH: 30
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (15)..(16)
<223> OTHER INFORMATION: n is a, c, g, or t

<400> SEQUENCE: 7

```
cattttttgct gccmnncagc ccacggcagg                                              30
```

<210> SEQ ID NO 8
<211> LENGTH: 30
<212> TYPE: DNA
<213> ORGANISM: Artificial Sequence
<220> FEATURE:
<223> OTHER INFORMATION: Oligonucleotide
<220> FEATURE:
<221> NAME/KEY: misc_feature
<222> LOCATION: (15)..(16)
<223> OTHER INFORMATION: n is a, c, g, or t

<400> SEQUENCE: 8

```
cctgccgtgg gctgnnkggc agcaaaaatg                                               30
```

<210> SEQ ID NO 9
<211> LENGTH: 216
<212> TYPE: PRT
<213> ORGANISM: Artificial Sequence
<220> FEATURE:
<223> OTHER INFORMATION: FcR9_F

<400> SEQUENCE: 9

Met Lys Ile Lys Thr Gly Ala Arg Ile Leu Ala Leu Ser Ala Leu Thr
1               5                   10                  15

Thr Met Met Phe Ser Ala Ser Ala Leu Ala Lys Ile Glu Glu Ala Met
            20                  25                  30

Gly Met Arg Thr Glu Asp Leu Pro Lys Ala Glu Val Ile Leu Glu Pro
        35                  40                  45

Gln Trp Asn Arg Val Leu Glu Lys Asp Ser Val Thr Leu Lys Cys Arg
    50                  55                  60

Gly Ala Tyr Ser Pro Glu Asp Asn Ser Thr Gln Trp Phe His Asn Glu
65                  70                  75                  80

Ser Leu Ile Ser Ser Gln Ala Ser Ser Tyr Leu Ile Asp Ala Ala Thr
                85                  90                  95

Val Asp Asp Ser Gly Glu Tyr Arg Cys Gln Thr Ser Leu Ser Thr Leu
            100                 105                 110

Ser Asp Pro Val Gln Leu Glu Val His Ile Gly Trp Leu Leu Leu Gln
        115                 120                 125

Ala Pro Arg Trp Glu Phe Lys Glu Gly Asp Pro Ile His Leu Arg Cys
    130                 135                 140

His Ser Trp Lys Asn Thr Ala Leu His Lys Val Thr Tyr Leu Gln Asn
145                 150                 155                 160

Gly Lys Gly Arg Lys Tyr Phe His His Asn Ser Asp Phe Tyr Ile Pro
                165                 170                 175

Lys Ala Thr Leu Lys Asp Ser Gly Ser Tyr Ser Cys Arg Gly Leu Phe
            180                 185                 190

Gly Ser Lys Asn Val Ser Ser Glu Thr Val Asn Ile Thr Ile Thr Gln
        195                 200                 205

Gly Gly His His His His His His
    210                 215

<210> SEQ ID NO 10
<211> LENGTH: 648
<212> TYPE: DNA
<213> ORGANISM: Artificial Sequence
<220> FEATURE:
<223> OTHER INFORMATION: Polynucleotide encoding FcR9_F

<400> SEQUENCE: 10

```
atgaaaataa aaacaggtgc acgcatcctc gcattatccg cattaacgac gatgatgttt    60
tccgcctcgg ctctcgccaa aatcgaagaa gccatgggca tgcgtaccga agatctgccg   120
aaagcggagg tgattctgga accgcagtgg aatcgcgtgc tggagaaaga ttctgtgacc   180
cttaaatgcc ggggcgcgta tagcccggaa gataacagca cccagtggtt ccacaatgaa   240
agcctgattt ccagccaggc gagcagctac cttattgatg cggcgacggt ggatgatagc   300
ggcgaatatc gttgccagac cagcctgagc accctgagcg atccggtgca gctggaggtg   360
cacatcgggt ggcttctgtt acaggctcca cggtgggagt tcaaagaggg ggatccgatt   420
catctgcggt gtcactcctg gaagaatacc gccctgcata agtgacctaa cctgcaaaac   480
ggcaagggcc gcaagtattt ccaccacaac tccgacttct atattcccaa agcgacgctg   540
aaggacagcg gcagctattc ctgccgtggg ctgttcggca gcaaaaatgt gagcagcgag   600
accgtgaata ttaccattac ccaaggggc catcatcatc atcatcat              648
```

<210> SEQ ID NO 11
<211> LENGTH: 37
<212> TYPE: DNA
<213> ORGANISM: Artificial Sequence
<220> FEATURE:
<223> OTHER INFORMATION: Oligonucleotide

<400> SEQUENCE: 11

```
tagccatggg catgcgtacc gaagatctgc cgaaagc                              37
```

<210> SEQ ID NO 12
<211> LENGTH: 66
<212> TYPE: DNA
<213> ORGANISM: Artificial Sequence
<220> FEATURE:
<223> OTHER INFORMATION: Oligonucleotide

<400> SEQUENCE: 12

```
cccaagctta tccgcaggta tcgttgcggc acccttgggt aatggtaata ttcacggtct    60
cgctgc                                                                66
```

<210> SEQ ID NO 13
<211> LENGTH: 19
<212> TYPE: DNA
<213> ORGANISM: Artificial Sequence
<220> FEATURE:
<223> OTHER INFORMATION: Oligonucleotide

<400> SEQUENCE: 13

```
tgtggtatgg ctgtgcagg                                                  19
```

<210> SEQ ID NO 14
<211> LENGTH: 18
<212> TYPE: DNA
<213> ORGANISM: Artificial Sequence
<220> FEATURE:
<223> OTHER INFORMATION: Oligonucleotide

<400> SEQUENCE: 14

```
tcggcatggg gtcaggtg                                                   18
```

<210> SEQ ID NO 15
<211> LENGTH: 207
<212> TYPE: PRT
<213> ORGANISM: Artificial Sequence
<220> FEATURE:

<223> OTHER INFORMATION: FcR9_F_Cys

<400> SEQUENCE: 15

```
Met Lys Tyr Leu Leu Ser Thr Ala Ala Ala Gly Leu Leu Leu Leu Ala
1               5                   10                  15
Ala Gln Pro Ala Met Ala Met Gly Met Arg Thr Glu Asp Leu Pro Lys
            20                  25                  30
Ala Glu Val Ile Leu Glu Pro Gln Trp Asn Arg Val Leu Glu Lys Asp
        35                  40                  45
Ser Val Thr Leu Lys Cys Arg Gly Ala Tyr Ser Pro Glu Asp Asn Ser
    50                  55                  60
Thr Gln Trp Phe His Asn Glu Ser Leu Ile Ser Gln Ala Ser Ser
65                  70                  75                  80
Tyr Leu Ile Asp Ala Ala Thr Val Asp Asp Ser Gly Glu Tyr Arg Cys
                85                  90                  95
Gln Thr Ser Leu Ser Thr Leu Ser Asp Pro Val Gln Leu Glu Val His
            100                 105                 110
Ile Gly Trp Leu Leu Leu Gln Ala Pro Arg Trp Glu Phe Lys Glu Gly
        115                 120                 125
Asp Pro Ile His Leu Arg Cys His Ser Trp Lys Asn Thr Ala Leu His
    130                 135                 140
Lys Val Thr Tyr Leu Gln Asn Gly Lys Gly Arg Lys Tyr Phe His His
145                 150                 155                 160
Asn Ser Asp Phe Tyr Ile Pro Lys Ala Thr Leu Lys Asp Ser Gly Ser
                165                 170                 175
Tyr Ser Cys Arg Gly Leu Phe Gly Ser Lys Asn Val Ser Ser Glu Thr
            180                 185                 190
Val Asn Ile Thr Ile Thr Gln Gly Cys Arg Asn Asp Thr Cys Gly
        195                 200                 205
```

<210> SEQ ID NO 16
<211> LENGTH: 621
<212> TYPE: DNA
<213> ORGANISM: Artificial Sequence
<220> FEATURE:
<223> OTHER INFORMATION: Polynucleotide encoding FcR9_F_Cys

<400> SEQUENCE: 16

```
atgaaatacc tgctgtcgac cgctgctgct ggtctgctgc tcctcgctgc ccagccggcg     60
atggccatgg gcatgcgtac cgaagatctg ccgaaagcgg aggtgattct ggaaccgcag    120
tggaatcgcg tgctggagaa agattctgtg acccttaaat gccggggcgc gtatagcccg    180
gaagataaca gcacccagtg gttccacaat gaaagcctga tttccagcca ggcgagcagc    240
taccttattg atgcggcgac ggtggatgat agcggcgaat atcgttgcca gaccagcctg    300
agcacccctga gcgatccggt gcagctggag gtgcacatcg gtggcttct gttacaggct    360
ccacggtggg agttcaaaga gggggatccg attcatctgc ggtgtcactc ctggaagaat    420
accgccctgc ataaagtgac ctacctgcaa acggcaagg gccgcaagta tttccaccac    480
aactccgact ctatattcc aaagcgacg ctgaaggaca gcggcagcta ttcctgccgt    540
gggctgttcg gcagcaaaaa tgtgagcagc gagaccgtga atattaccat acccaaggg    600
tgccgcaacg atacttgcgg a                                              621
```

<210> SEQ ID NO 17
<211> LENGTH: 451
<212> TYPE: PRT

<213> ORGANISM: Artificial Sequence
<220> FEATURE:
<223> OTHER INFORMATION: Rituximab Heavy chain

<400> SEQUENCE: 17

```
Gln Val Gln Leu Gln Gln Pro Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
        35                  40                  45

Gly Ala Ile Tyr Pro Gly Asn Gly Asp Thr Ser Tyr Asn Gln Lys Phe
50                  55                  60

Lys Gly Lys Ala Thr Leu Thr Ala Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala Ala Ser Thr Lys Gly Pro Ser
        115                 120                 125

Val Phe Pro Leu Ala Pro Ser Ser Lys Ser Thr Ser Gly Gly Thr Ala
130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
```

```
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
                420                 425                 430

His Glu Ala Leu His Asn His Tyr Thr Gln Lys Ser Leu Ser Leu Ser
                435                 440                 445

Pro Gly Lys
    450

<210> SEQ ID NO 18
<211> LENGTH: 213
<212> TYPE: PRT
<213> ORGANISM: Artificial Sequence
<220> FEATURE:
<223> OTHER INFORMATION: Rituximab Light chain

<400> SEQUENCE: 18

Gln Ile Val Leu Ser Gln Ser Pro Ala Ile Leu Ser Ala Ser Pro Gly
1               5                   10                  15

Glu Lys Val Thr Met Thr Cys Arg Ala Ser Ser Ser Val Ser Tyr Ile
                20                  25                  30

His Trp Phe Gln Gln Lys Pro Gly Ser Ser Pro Lys Pro Trp Ile Tyr
            35                  40                  45

Ala Thr Ser Asn Leu Ala Ser Gly Val Pro Val Arg Phe Ser Gly Ser
        50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 19
<211> LENGTH: 453
<212> TYPE: PRT
<213> ORGANISM: Artificial Sequence
<220> FEATURE:
<223> OTHER INFORMATION: Bevacizumab Heavy chain

<400> SEQUENCE: 19

Glu Val Gln Leu Val Glu Ser Gly Gly Gly Leu Val Gln Pro Gly Gly
1               5                   10                  15
```

```
Ser Leu Arg Leu Ser Cys Ala Ala Ser Gly Tyr Thr Phe Thr Asn Tyr
        20                  25                  30

Gly Met Asn Trp Val Arg Gln Ala Pro Gly Lys Gly Leu Glu Trp Val
        35                  40                  45

Gly Trp Ile Asn Thr Tyr Thr Gly Glu Pro Thr Tyr Ala Ala Asp Phe
50                      55                  60

Lys Arg Arg Phe Thr Phe Ser Leu Asp Thr Ser Lys Ser Thr Ala Tyr
65                  70                  75                  80

Leu Gln Met Asn Ser Leu Arg Ala Glu Asp Thr Ala Val Tyr Tyr Cys
                    85                  90                  95

Ala Lys Tyr Pro His Tyr Tyr Gly Ser Ser His Trp Tyr Phe Asp Val
                100                 105                 110

Trp Gly Gln Gly Thr Leu Val Thr Val Ser Ser Ala Ser Thr Lys Gly
            115                 120                 125

Pro Ser Val Phe Pro Leu Ala Pro Ser Ser Lys Ser Thr Ser Gly Gly
    130                 135                 140

Thr Ala Ala Leu Gly Cys Leu Val Lys Asp Tyr Phe Pro Glu Pro Val
145                 150                 155                 160

Thr Val Ser Trp Asn Ser Gly Ala Leu Thr Ser Gly Val His Thr Phe
                165                 170                 175

Pro Ala Val Leu Gln Ser Ser Gly Leu Tyr Ser Leu Ser Ser Val Val
            180                 185                 190

Thr Val Pro Ser Ser Ser Leu Gly Thr Gln Thr Tyr Ile Cys Asn Val
        195                 200                 205

Asn His Lys Pro Ser Asn Thr Lys Val Asp Lys Lys Val Glu Pro Lys
    210                 215                 220

Ser Cys Asp Lys Thr His Thr Cys Pro Pro Cys Pro Ala Pro Glu Leu
225                 230                 235                 240

Leu Gly Gly Pro Ser Val Phe Leu Phe Pro Pro Lys Pro Lys Asp Thr
                245                 250                 255

Leu Met Ile Ser Arg Thr Pro Glu Val Thr Cys Val Val Val Asp Val
            260                 265                 270

Ser His Glu Asp Pro Glu Val Lys Phe Asn Trp Tyr Val Asp Gly Val
        275                 280                 285

Glu Val His Asn Ala Lys Thr Lys Pro Arg Glu Glu Gln Tyr Asn Ser
    290                 295                 300

Thr Tyr Arg Val Val Ser Val Leu Thr Val Leu His Gln Asp Trp Leu
305                 310                 315                 320

Asn Gly Lys Glu Tyr Lys Cys Lys Val Ser Asn Lys Ala Leu Pro Ala
                325                 330                 335

Pro Ile Glu Lys Thr Ile Ser Lys Ala Lys Gly Gln Pro Arg Glu Pro
            340                 345                 350

Gln Val Tyr Thr Leu Pro Pro Ser Arg Glu Glu Met Thr Lys Asn Gln
        355                 360                 365

Val Ser Leu Thr Cys Leu Val Lys Gly Phe Tyr Pro Ser Asp Ile Ala
    370                 375                 380

Val Glu Trp Glu Ser Asn Gly Gln Pro Glu Asn Asn Tyr Lys Thr Thr
385                 390                 395                 400

Pro Pro Val Leu Asp Ser Asp Gly Ser Phe Phe Leu Tyr Ser Lys Leu
                405                 410                 415

Thr Val Asp Lys Ser Arg Trp Gln Gln Gly Asn Val Phe Ser Cys Ser
            420                 425                 430

Val Met His Glu Ala Leu His Asn His Tyr Thr Gln Lys Ser Leu Ser
```

```
            435                 440                 445

Leu Ser Pro Gly Lys
    450

<210> SEQ ID NO 20
<211> LENGTH: 214
<212> TYPE: PRT
<213> ORGANISM: Artificial Sequence
<220> FEATURE:
<223> OTHER INFORMATION: Bevacizumab Light chain

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys Ser Ala Ser Gln Asp Ile Ser Asn Tyr
            20                  25                  30

Leu Asn Trp Tyr Gln Gln Lys Pro Gly Lys Ala Pro Lys Val Leu Ile
        35                  40                  45

Tyr Phe Thr Ser Ser Leu His Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Thr Val Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Glu Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 21
<211> LENGTH: 1293
<212> TYPE: DNA
<213> ORGANISM: Artificial Sequence
<220> FEATURE:
<223> OTHER INFORMATION: Rituximab Heavy chain

<400> SEQUENCE: 21
caggtgcagc tgcaacaacc aggagctgaa ctcgtcaagc ctggcgccag cgtcaagatg      60
agttgtaagg catccggata cacatttact cctacaacat gcattgggt gaaacaaact     120 cctggaaggg ggctggaatg gatcggcgcc atctatcctg aaacggcga cacctcttac     180 aaccagaaat tcaagggcaa ggccaccctc accgctgaca atcttcttc tacagcttac     240 atgcagctga gctccctgac ctccgaagat tccgccgtat attactgtgc taggtccact     300
tattacggag gcgactggta tttaatgtc tggggagccg gcactacagt aaccgtttct     360
```

| | |
|---|---|
| gccgcatcca caaaaggccc ctccgtgttt cctctcgctc cttcatccaa aagtacttcc | 420 |
| ggtggtactg cagctctggg atgcctcgta aaagactatt ttccagaacc cgtcacagtc | 480 |
| tcctggaata gtggtgctct cacttccggc gtgcacacat tccctgccgt tctgcaaagc | 540 |
| agcgggctct atagcctgtc ttctgttgtg accgtgcctt ctagctctct tggtacccag | 600 |
| acttatatct gtaatgtgaa tcataagcca tctaatacca aggtggataa aaaagtcgag | 660 |
| cctaaaagtt gtgataagac acatacctgt cccccttgcc ctgctcctga gctcctggga | 720 |
| gggcctagcg tgtttctgtt tccccccaaag cccaaggaca ctctgatgat tagccggacc | 780 |
| ccagaagtga cctgcgtggt tgtggatgtc agccatgaag accccgaggt caaattcaac | 840 |
| tggtacgttg atggcgttga ggtccacaac gctaagacta gccccgcga agaacagtat | 900 |
| aaagagtaca atgcaaggt atctaataaa gccctgccag cacccattga aagaccata | 960 |
| agtaaagcaa agggtcagcc acgcgagccc caggtgtaca cattgccccc cagcagagat | 1020 |
| gagttgacca agaaccaggt gagcctgaca tgcctggtga agggttctta tccaagtgat | 1080 |
| attgcagtgg agtgggagag caatgggcag ccagagaaca actataagac cacccccca | 1140 |
| gtgcttgact cagatgggag ttctttcttg tacagtaagt tgacagtgga caagtcaaga | 1200 |
| tggcagcagg gaacgtgtt cagttgctca gtgatgcacg aggcacttca caaccactac | 1260 |
| acccagaagt cactttcact ttcaccaggg aag | 1293 |

<210> SEQ ID NO 22
<211> LENGTH: 639
<212> TYPE: DNA
<213> ORGANISM: Artificial Sequence
<220> FEATURE:
<223> OTHER INFORMATION: Rituximab Light chain

<400> SEQUENCE: 22

| | |
|---|---|
| cagatcgttt tgtcccaaag ccctgctatc ctgagcgcta gtcctggcga gaaagtgacc | 60 |
| atgacttgcc gcgcatcttc ttctgtgtcc tacatccatt ggtttcaaca aaaaccaggg | 120 |
| tcttccccca agccatggat atacgccact agcaacctgg cttctggtgt gcccgtgaga | 180 |
| ttctctggct ccggctccgg gacctcctac tctctgacta tctctagggt ggaagctgaa | 240 |
| gatgctgcca cttactattg tcagcagtgg acctcaaacc cccccacttt cggaggcggc | 300 |
| accaagctgg agatcaagcg gaccgtcgca gcaccaagcg tgtttatttt cccccccttca | 360 |
| gacgaacagc tgaaatcagg aacagccagc gtggtgtgtc tgcttaataa cttttatcca | 420 |
| agggaggcca aagttcagtg gaaggtcgat aatgccctcc agagcgggaa tagccaggag | 480 |
| tcagttacag aacaggacag caaggacagc acatatagtt tgtcatcaac cttgacccct | 540 |
| agtaaagccg actatgagaa gcacaaggtc tacgcatgcg aggtaacaca ccagggactc | 600 |
| agtagtcctg taacaaagag tttcaaccgt ggtgagtgc | 639 |

<210> SEQ ID NO 23
<211> LENGTH: 1359
<212> TYPE: DNA
<213> ORGANISM: Artificial Sequence
<220> FEATURE:
<223> OTHER INFORMATION: Bevacizumab Heavy chain

<400> SEQUENCE: 23

| | |
|---|---|
| gaagttcagc tggtggaatc gggaggcggc ttagtgcagc caggtgggtc tctgcgctta | 60 |
| tcgtgcgcag cctcgggcta taccttcacc aattatggca tgaactgggt gcgtcaggca | 120 |
| ccaggaaagg gtttagagtg ggtggggctgg attaatacct ataccggcga accgacctat | 180 |

```
gcagcggatt ttaagcgtcg tttttaccttt agcctggata ccagcaaaag cacagcgtat    240
ctgcaaatga atagtctgcg tgcggaagat acagccgtct attactgcgc gaaatacccg    300
cactattacg gctccagcca ttggtacttt gatgtgtggg gacaaggcac cctggtcacg    360
gtaagcagcg cgtcaaccaa aggcccgtca gtatttccgt tagcgcccag ctccaaatca    420
acatccgggg gtactgccgc gctgggctgt ctggtgaaag attatttccc tgaacctgtg    480
actgtgagct ggaatagcgg agcactgacc agcggggtgc atacttttcc ggccgtcttg    540
caatctagcg gcctgtattc cttgtctagc gtggtcactg tgccgagcag cagcctgggc    600
acacagacct acatttgtaa tgtgaatcat aaaccgagca acaccaaggt ggacaaaaaa    660
gtcgaaccca atcttgcga taaaacccat acgtgtccgc cgtgccccgc tccagaactg    720
ctgggtggcc cgagcgtgtt cctgtttccg ccgaaaccga aggataccct gatgattagc    780
cgtaccccgg aagtgacctg cgttgtggtg gatgtgagcc atgaagatcc ggaggtgaaa    840
ttcaactggt atgtggatgg cgtggaagtg cataacgcga aaaccaaacc gcgcgaagaa    900
cagtataact caacctaccg tgtggtgtca gtgttaaccg ttctgcacca agattggctg    960
aatggcaaag agtacaagtg caaagtgtcg aacaaagcgt taccagcgcc gattgaaaaa    1020
actatcagca aagcgaaagg gcagccgcgt gaaccgcagg tgtatacttt accgccgtct    1080
cgtgaagaaa tgacgaaaaa tcaggtgtcg cttacgtgct tggtaaaagg cttttatccc    1140
agcgatatag ccgtcgaatg ggaatcgaac ggccagccag aaaataacta caagaccaca    1200
cctccagtgc tggatagcga tggcagcttc tttctgtata gcaaactgac cgtagacaaa    1260
agccgttggc agcagggcaa cgtgtttagc tgtagcgtga tgcacgaagc tcttcataat    1320
cattataccc agaaatctct tagcttgtca ccgggtaaa                          1359
```

<210> SEQ ID NO 24
<211> LENGTH: 642
<212> TYPE: DNA
<213> ORGANISM: Artificial Sequence
<220> FEATURE:
<223> OTHER INFORMATION: Bevacizumab Light chain

<400> SEQUENCE: 24

```
gatattcaga tgacccagag cccgagcagc ctgagcgcgt ccgtgggcga tcgggtcacc     60
attacgtgta gcgcttctca ggatattagc aattatctga actggtatca gcagaaaccg    120
ggcaaagcgc ctaaagtgct gatctacttt accagctctc tgcatagcgg cgtgccgagc    180
cgttttagcg gcagcgggtc aggcaccgat ttcaccttga ccattagcag tctgcaaccg    240
gaagattttg cgacctatta ttgccagcag tattctaccg tgccgtggac ctttggccag    300
ggcacgaagg tagagattaa acgtaccgtg gccgctccca gcgtctttat ctttcccccg    360
agcgatgaac agctgaaaag cggcacagcg agcgtagtgt gcctgctgaa caatttctat    420
ccgcgtgaag cgaaagtgca atggaaggtg gataatgcgc tgcagagcgg aaatagccag    480
gaaagcgtga ccgaagaaga tagcaaggat agcacctata gcctgtcaag caccctgact    540
ctgagcaagg cggattacga aaaacataaa gtgtatgcgt gcgaagtgac ccatcagggg    600
ttaagctcgc cggtgaccaa aagcttcaat cgtggcgaat gc                       642
```

<210> SEQ ID NO 25
<211> LENGTH: 19
<212> TYPE: PRT
<213> ORGANISM: Artificial Sequence
<220> FEATURE:

-continued

<223> OTHER INFORMATION: Signal peptide for Heavy chain

<400> SEQUENCE: 25

Met Gly Trp Ser Leu Ile Leu Leu Phe Leu Val Ala Val Ala Thr Arg
1               5                   10                  15

Val Leu Ser

<210> SEQ ID NO 26
<211> LENGTH: 22
<212> TYPE: PRT
<213> ORGANISM: Artificial Sequence
<220> FEATURE:
<223> OTHER INFORMATION: Signal peptide for Light chain

<400> SEQUENCE: 26

Met Asp Phe Gln Val Gln Ile Ile Ser Phe Leu Leu Ile Ser Ala Ser
1               5                   10                  15

Val Ile Met Ser Arg Gly
            20

<210> SEQ ID NO 27
<211> LENGTH: 57
<212> TYPE: DNA
<213> ORGANISM: Artificial Sequence
<220> FEATURE:
<223> OTHER INFORMATION: Signal peptide for Heavy chain

<400> SEQUENCE: 27
atggggtgga gccttatcct tttgttttta gtggcggtgg cgacccgtgt gctgagc      57

<210> SEQ ID NO 28
<211> LENGTH: 66
<212> TYPE: DNA
<213> ORGANISM: Artificial Sequence
<220> FEATURE:
<223> OTHER INFORMATION: Signal peptide for Light chain

<400> SEQUENCE: 28
atggattttc aggtgcagat tattagcttt ctgttgatat cggcgtcggt gattatgagt      60
cgtgga      66

<210> SEQ ID NO 29
<211> LENGTH: 449
<212> TYPE: PRT
<213> ORGANISM: Artificial Sequence
<220> FEATURE:
<223> OTHER INFORMATION: anti-IL-6 Receptor antibody Heavy chain

<400> SEQUENCE: 29

Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

```
Ala Arg Ser Leu Ala Arg Thr Thr Ala Met Asp Tyr Trp Gly Gln Gly
            100                 105                 110

Ser Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 30
<211> LENGTH: 214
<212> TYPE: PRT
<213> ORGANISM: Artificial Sequence
<220> FEATURE:
<223> OTHER INFORMATION: anti-IL-6 Receptor antibody Light chain

<400> SEQUENCE: 30

Asp Ile Gln Met Thr Gln Ser Pro Ser Ser Leu Ser Ala Ser Val Gly
```

```
            1               5                  10                 15
Asp Arg Val Thr Ile Thr Cys Arg Ala Ser Gln Asp Ile Ser Ser Tyr
                20                  25                 30

Leu Asn Trp Tyr Gln Gln Lys Pro Gly Lys Ala Pro Lys Leu Leu Ile
            35                  40                 45

Tyr Tyr Thr Ser Arg Leu His Ser Gly Val Pro Ser Arg Phe Ser Gly
        50                  55                 60

Ser Gly Ser Gly Thr Asp Phe Thr Phe Thr Ile Ser Ser Leu Gln Pro
65                  70                  75                 80

Glu Asp Ile Ala Thr Tyr Tyr Cys Gln Gln Gly Asn Thr Leu Pro Tyr
                85                  90                 95

Thr Phe Gly Gln Gly Thr Lys Val Glu Ile Lys Arg Thr Val Ala Ala
            100                 105                110

Pro Ser Val Phe Ile Phe Pro Pro Ser Asp Glu Gln Leu Lys Ser Gly
            115                 120                125

Thr Ala Ser Val Val Cys Leu Leu Asn Asn Phe Tyr Pro Arg Glu Ala
        130                 135                140

Lys Val Gln Trp Lys Val Asp Asn Ala Leu Gln Ser Gly Asn Ser Gln
145                 150                 155                160

Glu Ser Val Thr Glu Gln Asp Ser Lys Asp Ser Thr Tyr Ser Leu Ser
                165                 170                175

Ser Thr Leu Thr Leu Ser Lys Ala Asp Tyr Glu Lys His Lys Val Tyr
            180                 185                190

Ala Cys Glu Val Thr His Gln Gly Leu Ser Ser Pro Val Thr Lys Ser
            195                 200                205

Phe Asn Arg Gly Glu Cys
    210
```

<210> SEQ ID NO 31
<211> LENGTH: 810
<212> TYPE: DNA
<213> ORGANISM: Artificial Sequence
<220> FEATURE:
<223> OTHER INFORMATION: dhfr+SV40

<400> SEQUENCE: 31

```
ccgcggatgg ttcgaccatt gaactgcatc gtcgccgtgt cccaaaatat ggggattggc      60
aagaacggag acctaccctg gcctccgctc aggaacgagt tcaagtactt ccaagaatg     120
accacaacct cttcagtgga aggtaaacag aatctggtga ttatgggtag aaaacctgg     180
ttctccattc ctgagaagaa tcgacctta aaggacagaa ttaatatagt tctcagtaga     240
gaactcaaag aaccaccacg aggagctcat tttcttgcca aaagtttgga tgatgcctta    300
agacttattg aacaaccgga attggcaagt aaagtagaca tggtttggat agtcggaggc    360
agttctgttt accaggaagc catgaatcaa ccaggccacc tcagactctt gtgacaagg     420
atcatgcagg aatttgaaag tgacacgttt tccccagaaa ttgatttggg aaatataaa     480
cttctcccag aatacccagg cgtcctctct gaggtccagg aggaaaaagg catcaagtat    540
aagtttgaag tctacgagaa gaaagactaa taaggcggcg gcgacatgat aagatacatt    600
gatgagtttg gacaaaccac aactagaatg cagtgaaaaa aatgctttat ttgtgaaatt    660
tgtgatgcta ttgctttatt tgtaaccatt ataagctgca ataaacaagt taacaacaac    720
aattgcattc attttatgtt tcaggttcag ggggagatgt gggaggtttt ttaaagcaag    780
taaaacctct acaaatgtgg taaaccgcgg                                     810
```

```
<210> SEQ ID NO 32
<211> LENGTH: 36
<212> TYPE: DNA
<213> ORGANISM: Artificial Sequence
<220> FEATURE:
<223> OTHER INFORMATION: Neo-Fsac

<400> SEQUENCE: 32
tccccgcggg cgggactctg gggttcgaaa tgaccg                                36

<210> SEQ ID NO 33
<211> LENGTH: 37
<212> TYPE: DNA
<213> ORGANISM: Artificial Sequence
<220> FEATURE:
<223> OTHER INFORMATION: Neo-Rsac

<400> SEQUENCE: 33
tccccgcggg gtggctctag ccttaagttc gagactg                               37

<210> SEQ ID NO 34
<211> LENGTH: 40
<212> TYPE: DNA
<213> ORGANISM: Artificial Sequence
<220> FEATURE:
<223> OTHER INFORMATION: CMV-forward

<400> SEQUENCE: 34
acgcgtcgac actagaagct ttattgcggt agtttatcac                            40

<210> SEQ ID NO 35
<211> LENGTH: 40
<212> TYPE: DNA
<213> ORGANISM: Artificial Sequence
<220> FEATURE:
<223> OTHER INFORMATION: CMV-reverse

<400> SEQUENCE: 35
acgcgtcgac agatctgtcg agccatgtga gcaaaaggcc                            40

<210> SEQ ID NO 36
<211> LENGTH: 45
<212> TYPE: DNA
<213> ORGANISM: Artificial Sequence
<220> FEATURE:
<223> OTHER INFORMATION: SV40pr-dhfr-SV40polyA-forward

<400> SEQUENCE: 36
tttaaatcag cggccgcgca gcaccatggc ctgaaataac ctctg                      45

<210> SEQ ID NO 37
<211> LENGTH: 48
<212> TYPE: DNA
<213> ORGANISM: Artificial Sequence
<220> FEATURE:
<223> OTHER INFORMATION: SV40pr-dhfr-SV40polyA-reverse

<400> SEQUENCE: 37
acgggcaccg gagcgatcgt ttaccacatt tgtagaggtt ttacttgc                   48

<210> SEQ ID NO 38
<211> LENGTH: 1265
<212> TYPE: DNA
<213> ORGANISM: Artificial Sequence
<220> FEATURE:
<223> OTHER INFORMATION: dhfr+SV40
```

<400> SEQUENCE: 38

```
gcagcaccat ggcctgaaat aacctctgaa agaggaactt ggttaggtac cttctgaggc      60
ggaaagaacc agctgtggaa tgtgtgtcag ttagggtgtg aaagtcccc aggctcccca     120
gcaggcagaa gtatgcaaag catgcatctc aattagtcag caaccaggtg tggaaagtcc    180
ccaggctccc cagcaggcag aagtatgcaa agcatgcatc tcaattagtc agcaaccata    240
gtcccgcccc taactccgcc catcccgccc taactccgc ccagttccgc ccattctccg      300
ccccatggct gactaatttt ttttatttat gcagaggccg aggccgcctc ggcctctgag    360
ctattccaga agtagtgagg aggctttttt ggaggcctag gcttttgcaa aaagcttgat    420
tcttctgaca caacagtctc gaacttaagg ctagagccac cccgcggatg gttcgaccat    480
tgaactgcat cgtcgccgtg tcccaaaata tggggattgg caagaacgga gacctaccct    540
ggcctccgct caggaacgag ttcaagtact tccaaagaat gaccacaacc tcttcagtgg    600
aaggtaaaca gaatctggtg attatgggta ggaaaacctg gttctccatt cctgagaaga    660
atcgaccttt aaaggacaga attaatatag ttctcagtag agaactcaaa gaaccaccac    720
gaggagctca ttttcttgcc aaaagtttgg atgatgcctt aagacttatt gaacaaccgg    780
aattggcaag taaagtagac atggtttgga tagtcggagg cagttctgtt taccaggaag    840
ccatgaatca accaggccac ctcagactct tgtgacaag gatcatgcag gaatttgaaa     900
gtgacacgtt tttcccagaa attgatttgg ggaaatataa acttctccca gaatacccag    960
gcgtcctctc tgaggtccag gaggaaaaag gcatcaagta taagtttgaa gtctacgaga   1020
agaaagacta ataaggcggc ggcgacatga taagatacat tgatgagttt ggacaaacca   1080
caactagaat gcagtgaaaa aaatgcttta tttgtgaaat ttgtgatgct attgctttat   1140
ttgtaaccat tataagctgc aataaacaag ttaacaacaa caattgcatt cattttatgt   1200
ttcaggttca gggggagatg tgggaggttt tttaaagcaa gtaaaacctc tacaaatgtg   1260
gtaaa                                                               1265
```

<210> SEQ ID NO 39
<211> LENGTH: 119
<212> TYPE: PRT
<213> ORGANISM: Artificial Sequence
<220> FEATURE:
<223> OTHER INFORMATION: anti-IL-6 Receptor antibody Heavy chain VR

<400> SEQUENCE: 39

```
Gln Val Gln Leu Gln Glu Ser Gly Pro Gly Leu Val Arg Pro Ser Gln
1               5                   10                  15

Thr Leu Ser Leu Thr Cys Thr Val Ser Gly Tyr Ser Ile Thr Ser Asp
            20                  25                  30

His Ala Trp Ser Trp Val Arg Gln Pro Pro Gly Arg Gly Leu Glu Trp
        35                  40                  45

Ile Gly Tyr Ile Ser Tyr Ser Gly Ile Thr Thr Tyr Asn Pro Ser Leu
    50                  55                  60

Lys Ser Arg Val Thr Met Leu Arg Asp Thr Ser Lys Asn Gln Phe Ser
65                  70                  75                  80

Leu Arg Leu Ser Ser Val Thr Ala Ala Asp Thr Ala Val Tyr Tyr Cys
                85                  90                  95

Ala Arg Ser Leu Ala Arg Thr Thr Ala Met Asp Tyr Trp Gly Gln Gly
            100                 105                 110

Ser Leu Val Thr Val Ser Ser
```

```
<210> SEQ ID NO 40
<211> LENGTH: 370
<212> TYPE: DNA
<213> ORGANISM: Artificial Sequence
<220> FEATURE:
<223> OTHER INFORMATION: signal peptide_anti-IL6 Receptor antibody heavy
      chain VR

<400> SEQUENCE: 40
gaattcgcag gtgcagttgc aggagtccgg ccctggtctg gttaggccct cccagaccct      60
gtccctgacc tgcaccgtgt ccggctactc catcacctcc gaccacgcct ggtcatgggt     120
gaggcagccc ccaggcaggg gcctggagtg gatcggctac atctcctact ccggcatcac     180
cacctacaac ccctccctga gtccaggggt gaccatgctg cgcgacacct ccaagaacca     240
gttctccctt cggctgtcct ccgtgaccgc cgctgacacc gccgtgtact actgcgccag     300
gtcccttgcc aggaccactg ccatggacta ctggggccag ggctccctgg tgaccgtctc     360
ctccgctagc                                                            370

<210> SEQ ID NO 41
<211> LENGTH: 108
<212> TYPE: PRT
<213> ORGANISM: Artificial Sequence
<220> FEATURE:
<223> OTHER INFORMATION: anti-IL-6 Receptor antibody Light chain VR

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Ser Ser Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

Glu Asp Ile Ala Thr Tyr Tyr Cys Gln Gln Gly Asn Thr Leu Pro Tyr
                85                  90                  95

Thr Phe Gly Gln Gly Thr Lys Val Glu Ile Lys Arg
            100                 105

<210> SEQ ID NO 42
<211> LENGTH: 334
<212> TYPE: DNA
<213> ORGANISM: Artificial Sequence
<220> FEATURE:
<223> OTHER INFORMATION: signal peptide_anti-IL6 Receptor antibody light
      chain VR

<400> SEQUENCE: 42
gaattcagat attcaaatga cccagagccc gagctctctg agcgcgagcg tgggcgatcg      60
tgtgaccatt acttgccgtg cgagccagga tatttccagc tatctgaatt ggtatcagca     120
aaaaccgggc aaagcgccga aactgctgat ttactatacc agccgtctgc atagcggcgt     180
```

```
gccgagccgt tttagcggga gcggcagcgg caccgatttt acctttacca ttagcagcct      240
gcagccggaa gatattgcga cctattattg ccagcagggc aataccctgc cgtataccat      300
tggccagggc accaaagtgg aaattaagcg tacg                                  334
```

FC-BINDING PROTEIN HAVING IMPROVED ANTIBODY SEPARATION ABILITY, AND METHOD FOR SEPARATING ANTIBODY USING SAME

SEQUENCE LISTING

The instant application contains a Sequence Listing which has been filed electronically in ASCII format and is hereby incorporated by reference in its entirety. Said ASCII copy, created on Feb. 24, 2020, is named Sequence Listing4.txt and is 47,206 bytes in size.

FIELD

The present invention relates to an Fc-binding protein having improved antibody (immunoglobulin) separation ability, and a method for separating an antibody using the same. More specifically, the present invention relates to an Fc-binding protein which has decreased affinity to an antibody as compared to a conventionally known Fc-binding protein so as to have improved antibody (immunoglobulin) separation ability, and a method for separating an antibody using an insoluble carrier having the Fc-binding protein immobilized thereon.

BACKGROUND

The sugar chain structure of an antibody drug plays a major role in drug efficacy and stability. It is therefore extremely important to control the sugar chain structure when producing an antibody drug. Among Fc-binding proteins, FcγRIIIa is known to recognize the sugar chain structure of an antibody (immunoglobulin). The antibody can be separated based on the sugar chain structure by using an adsorbent obtained by immobilizing FcγRIIIa on an insoluble carrier (PTL 1). Accordingly, the adsorbent is useful for step analysis and isolation upon antibody drug production.

Meanwhile, it is known that FcγRIIIa has lower antibody-binding ability as compared to another Fc-binding protein, namely, FcγRI (NPL 1), and the affinity to an antibody is improved by introducing a mutation into a protein having antibody-binding ability (PTL 2). However, the degree of separation of an antibody has not been improved. Meanwhile, the site of interaction between the Fc-binding protein and the antibody has been clarified (NPL 2), and amino acid residues involved in binding between the Fc-binding protein and the antibody have been revealed. However, such findings are not enough to improve the degree of separation in relation to antibody analysis and adsorption. Therefore, in the industrial production of antibody drugs, it was difficult to apply an FcγRIIIa-immobilized carrier to step analysis and product analysis.

CITATION LIST

Patent Literature

[PTL 1] Japanese Unexamined Patent Publication (Kokai) No. 2015-086216

[PTL 2] Japanese Unexamined Patent Publication (Kokai) No. 2015-019615

Non Patent Literature

[NPL 1] P. Bruhns et al., Blood, 16, 3716-3725, 2009
[NPL 2] P. Sonderman et al., Nature, 406, 267-2735, 2000

SUMMARY

Technical Problem

According to the present invention, an Fc-binding protein having improved antibody (immunoglobulin) separation ability as compared to a conventionally known Fc-binding protein is provided, and a method for separating an antibody (immunoglobulin) with high accuracy using an insoluble carrier having the protein immobilized thereon is provided.

Solution to Problem

In order to solve the above problems, the present inventors conducted exhaustive substitutions of a specific amino acid residue in FcγRIIIa involved in antibody-binding ability. As a result, Fc-binding proteins having decreased affinity to an antibody was obtained by substituting the amino acid residue by a different amino acid residue. In addition, the use of a carrier having the protein immobilized thereon has made it possible to separate an antibody with high accuracy as compared to an insoluble carrier having a conventional Fc-binding protein immobilized thereon. Specifically, among amino acid residues involved in antibody-binding ability in an Fc-binding protein consisting of the amino acid sequence set forth in SEQ ID NO: 5 (human FcγRIIIa amino acid substitution product), exhaustive substitutions of the amino acid corresponding to valine at position 192 of SEQ ID NO: 5 (corresponding to valine at position 176 in natural human FcγRIIIa consisting of the amino acid sequence set forth in SEQ ID NO: 1) by different amino acids were conducted. Accordingly, an Fc-binding protein having decreased affinity to an antibody as compared to an Fc-binding protein consisting of the amino acid sequence set forth in SEQ ID NO: 5 was obtained, and the use of an insoluble carrier having the protein immobilized thereon has made it possible to separate the antibody with high accuracy as compared to an insoluble carrier having a conventional Fc-binding protein immobilized thereon.

In other words, the present invention encompasses embodiments described in the following (1) to (7).

(1) An Fc-binding protein comprising at least amino acid residues at positions 33 to 208 of the amino acid sequence set forth in SEQ ID NO: 5, wherein among the amino acid residues at positions 33 to 208, at least valine at position 192 is amino acid-substituted by phenylalanine.

(2) The Fc-binding protein according to (1), which is selected from among the following (a), (b), and (c):

(a) an Fc-binding protein in which among amino acid residues at positions 33 to 208 of the amino acid sequence set forth in SEQ ID NO: 5, valine at position 192 is amino acid-substituted by phenylalanine;

(b) an Fc-binding protein in which among amino acid residues at positions 33 to 208 of the amino acid sequence set forth in SEQ ID NO: 5, valine at position 192 is amino acid-substituted by phenylalanine, and which further comprises an amino acid residue having a substitution, deletion, insertion, or addition of one or more amino acids, and which has antibody-binding activity; and (c) an Fc-binding protein which has 80% or more homology to an amino acid sequence comprising amino acid residues from glycine at position 33 to glutamine at position 208 of the amino acid sequence set forth in SEQ ID NO: 4, in which valine at position 192 is amino acid-substituted by phenylalanine, and which has antibody-binding activity.

(3) A method for separating an antibody, comprising: a step of adding an equilibration solution to a column which is filled with an insoluble carrier having the Fc-binding protein according to (1) or (2) immobilized thereon so as to equilibrate the column; a step of adding a solution containing an antibody to cause the antibody to be adsorbed on the carrier; and a step of eluting the antibody adsorbed on the carrier using an elution solution.

(4) The separation method according to (3), further comprising a step of isolating a fraction containing the eluted antibody.

(5) The separation method according to (3) or (4), wherein the equilibration solution is a buffer containing an inorganic salt at pH 4.5 to pH 5.8.

(6) A method for monitoring culture progress of an antibody-producing cell and a produced antibody, comprising: a step of obtaining an antibody-producing cell by transfecting a host cell with an antibody expression vector; a step of culturing the antibody-producing cell; a step of obtaining an antibody from the culture solution; and a step of separating the obtained antibody by the method according to any one of (3) to (5).

(7) A method for monitoring time-dependent changes in a sugar chain structure pattern of an antibody, comprising: a step of obtaining an antibody-producing cell by transfecting a host cell with an antibody expression vector; a step of culturing the antibody-producing cell; a step of obtaining an antibody from the culture medium and/or cultured cells; and a step of separating the obtained antibody by the method according to any one of (3) to (5).

(8) A method for producing an antibody, comprising a step of optimizing culture conditions for an antibody-producing cell based on the results of monitoring by the method according to (7) such that the cell produces an antibody having a desired sugar chain structure.

Hereinafter, the present invention will be described in detail.

Specifically, the separation of an antibody may include not only separation of an antibody from contaminants but also separation between antibodies based on the structure, properties, activity, and the like.

The Fc-binding protein of the present invention is a protein having ability to bind to the Fc region of an antibody (immunoglobulin), which includes amino acid residues from glycine at position 33 to glutamine at position 208 of SEQ ID NO: 5 (corresponding to a region at least from glycine at position 17 to glutamine at position 192 in the extracellular domain (the region of EC in FIG. 1) of natural human FcγRIIIa consisting of the amino acid sequence set forth in SEQ ID NO: 1), and which has at least an amino acid substitution of an amino acid residue at a certain position among the amino acid residues at positions 33 to 208. Therefore, an Fc-binding protein used in the present invention may include all or part of a signal peptide region (S in FIG. 1) present on the N-terminal side of the extracellular domain, or it may include all or part of a transmembrane domain (TM in FIG. 1) and an intracellular domain (C in FIG. 1) present on the C-terminal side of the extracellular domain. Specifically, an amino acid substitution at the certain position is an amino acid substitution denoted by Val192Phe (indicating a substitution of valine at position 192 of SEQ ID NO: 5 (corresponding to position 176 of SEQ ID NO: 1) by phenylalanine, and so forth).

There is a known variant of wild-type FcγRIIIa, which has an amino acid substitution of at least one of Leu82His, Leu82Arg, Gly163Asp, and Tyr174His. The Fc-binding protein of the present invention may have such an amino acid substitution, in addition to an amino acid substitution (Val192Phe) at the certain position.

When the Fc-binding protein of the present invention is produced via amino acid substitution, an amino acid residue at a certain position may be substituted by an amino acid other than the above-described amino acid as long as the protein has antibody-binding activity. Specifically, the protein may have at least one of substitution, deletion, insertion, and addition of one or more amino acid residues. The expression "one or more" or "at least one" may refer to, for example, from 1 to 50, preferably form 1 to 40, more preferably from 1 to 30, still more preferably form 1 to 20, particularly preferably form 1 to 10, although it depends on positions and types of amino acid residues in the protein conformation. One example of a substitution, deletion, insertion, or addition of one or more amino acid residues is a conservative substitution between amino acids having similar physical and/or chemical properties. Those skilled in the art know that in the case of conservative substitution, the protein function is usually maintained between a protein having a substitution and a protein lacking the substitution, each of which is not limited to an Fc-binding protein. One example of a conservative substitution is a substitution that occurs between glycine and alanine, aspartic acid and glutamic acid, serine and proline, or glutamic acid and alanine (Protein Structure and Function, Medical Sciences International, Ltd., 9, 2005).

In addition, the Fc-binding protein of the present invention may be an Fc-binding protein having amino acid residues including Val192Phe described above which have 70% or more, preferably 80% or more, still more preferably 90% or more, particularly preferably 95% or more amino acid sequence homology to amino acid residues from glycine at position 33 to glutamine at position 208 of SEQ ID NO: 5 as long as the Fc-binding protein has antibody-binding activity.

A specific example of the Fc-binding protein of the present invention is an Fc-binding protein which includes at least amino acid residues at positions 33 to 208 of the amino acid sequence set forth in SEQ ID NO: 5, and has at least an amino acid substitution of Val192Phe in the amino acid residues at positions 33 to 208 (polypeptide at least including a region of amino acid residues at positions 33 to 208 of the amino acid sequence of SEQ ID NO: 9).

It is possible to further add a useful oligopeptide to the N-terminal side or the C-terminal side of the Fc-binding protein of the present invention when separating an antibody of interest from a solution with the presence of contaminants. Examples of the oligopeptide include polyhistidine, polylysine, polyarginine, polyglutamic acid, and polyaspartic acid. Further, a cysteine-containing oligopeptide, which is useful for immobilizing the Fc-binding protein of the present invention to a solid phase of a support for chromatography or the like, may be further added to the N-terminal side or the C-terminal side of the Fc-binding protein of the present invention. The length of an oligopeptide to be added to the N-terminal side or the C-terminal side of the Fc-binding protein is not particularly limited. When adding the oligopeptide to the Fc-binding protein of the present invention, it is possible to prepare a polynucleotide encoding the oligopeptide, and then, add the polynucleotide to the N-terminal side or the C-terminal side of the Fc-binding protein by a genetic engineering method known to those skilled in the art. Alternatively, it is also possible to chemically synthesize the oligopeptide and add the oligopeptide to the N-terminal side or the C-terminal side of the Fc-binding protein of the present invention via chemical binding. It is also possible to further add a signal peptide to the N-terminal side of the Fc-binding protein of the present invention for promoting efficient expression in a host. Examples of the signal peptide when a host is *Escherichia coli* include signal peptides that cause protein secretion in a periplasmic space, such as, PelB, DsbA, MalE (a region of the 1st to 26th amino acid residues of the amino acid sequence described in UniProt No. P0AEX9), and TorT (Japanese Unexamined Patent Publication (Kokai) No. 2011-097898).

When separating or analyzing an antibody using the Fc-binding protein of the present invention, it is necessary to prepare an antibody adsorbent in which the Fc-binding protein of the present invention is immobilized on an insoluble carrier as described above. An insoluble carrier to be immobilized to the Fc-binding protein is not particularly limited. Examples thereof include carriers made with polysaccharides such as agarose, alginate (alginic acid salt), carrageenan, chitin, cellulose, dextrin, dextran, and starch, carriers made with synthetic polymers such as polyvinyl alcohol, polymethacrylate, poly (2-hydroxyethyl methacrylate), and polyurethane, and carriers made with ceramics such as silica. Of these, carriers made with polysaccharides and carriers made with synthetic polymers are preferable as insoluble carriers. Examples of the preferable carrier include hydroxylated polymethacrylate gel such as TOYOPEARL (manufactured by Tosoh Corporation), agarose gel such as Sepharose® (manufactured by GE Healthcare), and cellulose gel such as Cellufine (manufactured by JNC). The shape of insoluble carrier is not particularly limited, and it may be either a particulate or non-particulate shape or a porous or nonporous shape.

In order to immobilize the Fc-binding protein of the present invention on an insoluble carrier, it is possible to provide the insoluble carrier with an active group such as an N-hydroxysuccinimide (NHS)-activated ester group, an epoxy group, a carboxyl group, a maleimide group, a haloacetyl group, a tresyl group, a formyl group, or haloacetamide and allow the Fc-binding protein of the present invention to covalently bind to the insoluble carrier via the active group. It is possible to directly use a commercially available carrier as a carrier provided with an active group or to prepare a carrier by introducing an active group to the carrier surface under appropriate reaction conditions. Examples of a commercially available carrier provided with an active group include TOYOPEARL AF-Epoxy-650M, TOYOPEARL AF-Tresyl-650M (each manufactured by Tosoh Corporation), HiTrap® NETS-activated HP Columns, NETS-activated Sepharose® 4 Fast Flow, Epoxy-activated Sepharose® 6B (each manufactured by GE Healthcare), and SulfoLink™ Coupling Resin (manufactured by Thermo Fisher Scientific).

Meanwhile, as a method for introducing an active group on the carrier surface, a method in which a compound having two or more active sites is allowed to react, at one of the active sites, with a hydroxyl group, an epoxy group, a carboxyl group, an amino group, or the like present on the carrier surface can be exemplified. Among examples of such a compound, examples of a compound for introducing an epoxy group to a hydroxyl group or an amino group on the carrier surface include epichlorohydrin, ethanediol diglycidyl ether, butanediol diglycidyl ether, and hexanediol diglycidyl ether. Examples of a compound for introducing a carboxyl group on the carrier surface after introduction of an epoxy group on the carrier surface by the compound include 2-mercaptoacetic acid, 3-mercaptopropionic acid, 4-mercaptobutyric acid, 6-mercaptobutyric acid, glycine, 3-aminopropionic acid, 4-aminobutyric acid, and 6-aminohexanoic acid.

Examples of a compound for introducing a maleimide group to a hydroxyl group, an epoxy group, a carboxyl group, or an amino group present on the carrier surface include N-(ε-maleimidocaproic acid)hydrazide, N-(ε-maleimidopropionic acid)hydrazide, 4-(4-N-maleimidophenyl) acetic acid hydrazide, 2-aminomaleimide, 3-aminomaleimide, 4-aminomaleimide, 6-aminomaleimide, 1-(4-aminophenyl)maleimide, 1-(3-aminophenyl)maleimide, 4-(maleimide)phenyl isocyanate, 2-maleimidoacetic acid, 3-maleimidopropionic acid, 4-maleimidobutyric acid, 6-maleimidohexanoic acid, N-(α-maleimidoacetoxy)succinimide ester, (m-maleimidobenzoyl)N-hydroxy succinimide ester, succinimidyl-4-(maleimidomethyl)cyclohexane-1-carbonyl-(6-aminohexanoic acid), succinimidyl-4-(maleimidomethyl)cyclohexane-1-carboxylic acid, (p-maleimidobenzoyl) N-hydroxy succinimide ester, and (m-maleimidobenzoyl)N-hydroxy succinimide ester.

Examples of a compound for introducing a haloacetyl group to a hydroxyl group or an amino group present on the carrier surface include chloroacetic acid, bromoacetic acid, iodoacetic acid, chloroacetic acid chloride, bromoacetic acid chloride, bromoacetic acid bromide, chloroacetic acid anhydride, bromoacetic acid anhydride, iodoacetic acid anhydride, 2-(iodoacetamido)acetic acid-N-hydroxysuccinimide ester, 3-(bromoacetamido)propionic acid-N-hydroxysuccinimide ester, and 4-(iodoacetyl)aminobenzoic acid-N-hydroxysuccinimide ester. A method in which ω-alkenyl alkane glycidyl ether is reacted with a hydroxyl group or an amino group present on the carrier surface, and then, ω-alkenyl is halogenated with a halogenating agent for activation can also be exemplified. Examples of ω-alkenyl alkane glycidyl ether may include allyl glycidyl ether, 3-butenyl glycidyl ether, and 4-pentenyl glycidyl ether. Examples of a halogenating agent may include N-hlorosuccinimide, N-bromosuccinimide, and N-iodosuccinimide.

Another example of a method for introducing an active group on the carrier surface is a method for introducing an active group to a carboxyl group present on the carrier surface using a condensing agent and an additive. Examples of a condensing agent include 1-ethyl-3-(3-dimethylaminopropyl)carbodiimide (EDC), dicyclohexylcarbodiamide, and carbonyldiimidazole. Examples of an additive include N-hydroxysuccinimide (NHS), 4-nitrophenol, and 1-hydroxybenzotriazole.

Examples of a buffer used for immobilizing the Fc-binding protein of the present invention on an insoluble carrier include acetate buffer, phosphate buffer, MES (2-morpholinoethanesulfonic acid) buffer, HEPES (4-(2-hydroxyethyl)-1-piperazineethanesulfonic acid) buffer, Tris buffer, and boric acid buffer. The reaction temperature for immobilization may be set as appropriate in a temperature range of from 5° C. to 50° C., preferably from 10° C. to 35° C., in consideration of reactivity of an active group and stability of an Fc-binding protein.

In order to carry out the separation method of the present invention using an antibody adsorbent obtained by the above-described method, an antibody may be eluted by adding a solution containing the antibody to a column filled with the antibody adsorbent using liquid transfer means such as a pump to allow the adsorbent to specifically adsorb the antibody, and then, adding an appropriate elution solution to the column. It is favorable to treat the solution containing an antibody by solvent substitution using an appropriate buffer before adding the solution to the column. In addition, it is preferable to equilibrate the column using an appropriate buffer before adding the solution containing an antibody to the column such that the antibody can be separated with high purity. Examples of a buffer used for equilibration (equilibration solution) include phosphate buffer, acetate buffer, and MES buffer. It is also possible to further add an inorganic salt such as 10 mM to 100 mM (preferably 40 mM to 60 mM) sodium chloride to the buffer. The pH of an equilibration solution is usually pH 3.0 to 5.8, preferably pH 4.5 to 5.8, more preferably pH 5.2 to pH 5.7 because the Examples described later indicate that when the pH is 6.0 or more, antibody separation ability of an antibody adsorbent to which the Fc-binding protein of the present invention is bound to largely declines. In order to elute the antibody adsorbed by the antibody adsorbent, it is favorable to reduce interaction between the antibody and the ligand (the Fc-binding protein of the present invention). Specifically, reducing pH using buffer, adding a counter peptide, increasing temperature, and changing salt concentration can be exemplified. Examples of an elution solution for eluting the antibody adsorbed by the antibody adsorbent, a buffer having a pH more acidic than that of the solution used for allowing the antibody adsorbent to adsorb the antibody can be exemplified. Examples of such a buffer include citrate buffer, glycine-HCl buffer, and acetate buffer, which have buffer capacity on the acidic side. The pH of buffer may be set in a range that does not impair the function (such as antigen-binding ability) possessed by the antibody, and it is preferably pH 2.5 to 6.0, more preferably pH 3.0 to 5.0, still more preferably pH 3.3 to 4.0.

Further, it is possible to isolate a fraction containing the eluted antibody, thereby collecting the antibody from the obtained fraction. Isolation may be carried out by an ordinary method. Specifically, for example, the fraction can be isolated by a method including replacing a collection container every fixed time or fixed capacity, a method including replacing a collection container according to the shape of an elution solution chromatogram, and a method using an automated fraction collector such as autosampler.

As means for obtaining an antibody of interest in the field of antibody drugs, culturing cells capable of producing an antibody of interest (hereinafter referred to as "antibody-producing cells") and collecting the antibody of interest from the culture solution (culture medium and/or antibody-producing cells) can be exemplified. A method for obtaining antibody-producing cells can be carried out by, for example, preparing an expression vector including DNA encoding all or part of the heavy chain and/or light chain of an antibody (hereinafter referred to as "antibody expression vector") and introducing the expression vector into a host cell. A host cell into which the antibody expression vector is introduced can be a cell capable of stably expressing a protein. Examples thereof include animal cells, insect cells, plant cells, eukaryotic cells, and prokaryotic cells. However, in view of efficiency of antibody production, animal cells are preferable. Further, COS cells (African green monkey kidney-derived cells), CHO cells (Chinese hamster ovary cells), Sp2/0 cells and NS0 cells (mouse myeloma cells) are more preferable.

Advantageous Effects of Invention

The Fc-binding protein of the present invention has decreased affinity to an antibody as compared with a conventional Fc-binding protein (specifically, an amino acid substitution product of human FcγRIIIa consisting of the amino acid sequence set forth in SEQ ID NO: 5). Therefore, according to the present invention, accuracy in process analysis of an antibody and separation efficiency in isolating an antibody with the use of an Fc-binding protein-immobilized carrier can be improved.

Further, the Fc-binding protein of the present invention is an amino acid substitution product (variant) of FcγRIIIa, and an adsorbent obtained by immobilizing FcγRIIIa on an insoluble carrier is capable of separating an antibody based on the sugar chain structure (Japanese Unexamined Patent Publication (Kokai) No. 2015-086216). Moreover, separation using the adsorbent enables separation based on the degree of antibody dependent cellular cytotoxicity (Japanese Unexamined Patent Publication (Kokai) No. 2016-23152). Therefore, it can be said that the present invention is particularly useful for process analysis and isolation of antibody drugs.

For example, in the culture of antibody-producing cells, by separating an antibody contained in the culture solution during culture based on the sugar chain structure by the separation method of the present invention, process analysis for monitoring culture progress and the sugar chain structure pattern of a produced antibody can be readily carried out. Based on the results of monitoring the sugar chain structure pattern, culture conditions for producing an antibody drug having an optimal sugar chain structure can also be readily set. In addition, as it is possible to predict a sugar chain structure based on a purified antibody separation pattern obtained using the present invention, the present invention is also useful for quality control and quality analysis of antibody drugs.

BRIEF DESCRIPTION OF DRAWINGS

FIG. 1 schematically illustrates human FcγRIIIa. The numerals in FIG. 1 correspond to positions in the amino acid sequence set forth in SEQ ID NO: 1. In FIG. 1, S represents a signal sequence, EC represents an extracellular domain, TM represents a transmembrane domain, and C represents an intracellular domain.

FIG. 2 depicts an elution pattern (chromatogram) when a monoclonal antibody was separated using a column filled with an insoluble carrier having the Fc-binding protein of the present invention (FcR9_F) immobilized thereon.

FIG. 3 depicts an elution pattern (chromatogram) when a monoclonal antibody was separated using a column filled with an insoluble carrier having a conventional Fc-binding protein (FcR9) immobilized thereon.

EXAMPLES

Figure 4:
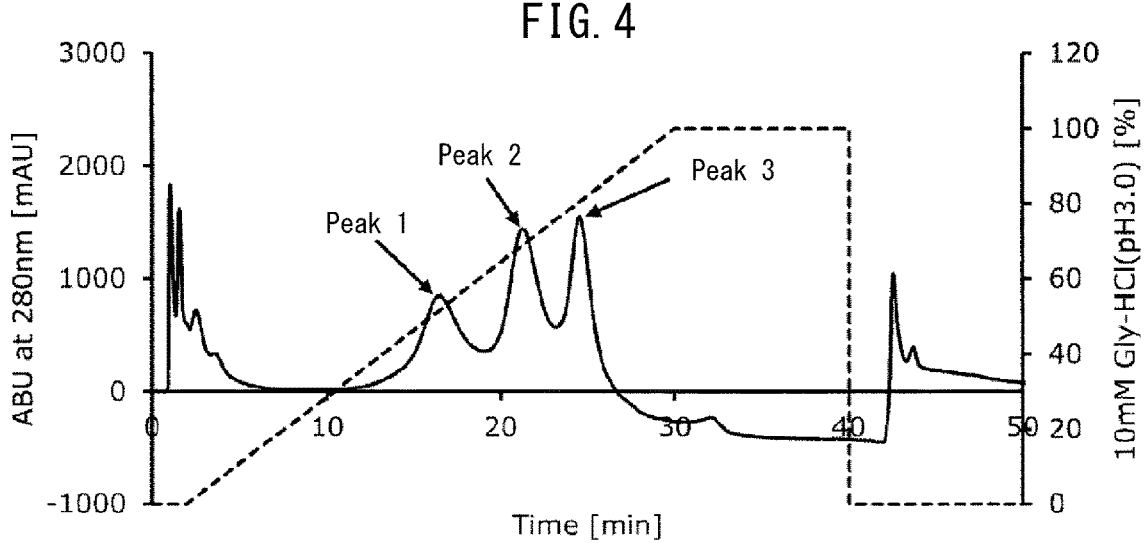
FIG. 4 depicts an elution pattern (chromatogram) when the pH of an equilibration buffer was set to 5.5 in Example 6.

Hereinafter, the present invention will be described in more detail with reference to the Examples below, but the present invention is not limited to these Examples.

Example 1 Preparation of FcR9 Amino Acid Substitution Product

An amino acid substitution was introduced into an Fc-binding protein FcR9 (SEQ ID NO: 5) prepared in accordance with the method disclosed in WO2015/199154 as described below in order to confirm usefulness of a substitution of valine at position 192 (corresponding to valine at position 176 in wildtype human FcγRIIIa consisting of the amino acid sequence set forth in SEQ ID NO: 1) by a different amino acid. Specifically, an amino acid substitution was introduced into plasmid pET-FcR9 (WO2015/199154) including a polynucleotide (SEQ ID NO: 6) encoding FcR9 by PCR, thereby producing an Fc-binding protein having a substitution of valine at position 192 in FcR9 (SEQ ID NO: 5) by a different amino acid. FcR9 (SEQ ID NO: 5) is an Fc-binding protein including the wild-type FcγRIII extracellular domain set forth in SEQ ID NO: 4, which has an amino acid substitution of Val at position 43 by Glu (corresponding to position 27 of SEQ ID NO: 1), an amino acid substitution of Phe at position 45 by Ile (corresponding to position 29 of SEQ ID NO: 1), an amino acid substitution of Tyr at position 51 by Asn (corresponding to position 35 of SEQ ID NO: 1), an amino acid substitution of Gln at position 64 by Arg (corresponding to position 48 of SEQ ID NO: 1), an amino acid substitution of Phe at position 91 by Leu (corresponding to position 75 of SEQ ID NO: 1), an amino acid substitution of Asn at position 108 by Ser (corresponding to position 92 of SEQ ID NO: 1), an amino acid substitution of Val at position 133 by Glu (corresponding to position 117 of SEQ ID NO: 1), an amino acid substitution of Glu at position 137 by Gly (corresponding to position 121 of SEQ ID NO: 1), and an amino acid substitution of Phe at position 187 by Ser (corresponding to position 171 of SEQ ID NO: 1).

Hereinafter, a method for producing the following Fc-binding proteins will be described in detail.

(1) In order to confirm usefulness of a substitution of valine at position 192 (corresponding to position 176 in SEQ ID NO: 1) in the Fc-binding protein FcR9 (SEQ ID NO: 5) by a different amino acid, a reaction solution having the composition in Table 1 was prepared using plasmid pET-FcR9 (disclosed in WO2015/199154) including the polynucleotide (SEQ ID NO: 6) encoding FcR9 (SEQ ID NO: 5) produced by the method disclosed in WO2015/199154 as a template and oligoprimers consisting of the sequences set forth in SEQ ID NO: 2 (5'-TAATACGACTCACTATAGGG-3') and SEQ ID NO: 7 (5'-CATTTTTGCTGCCMNNCAGCCCACGGCAGG-3'). Subsequently, the reaction solution was heat-treated at 95° C. for 2 minutes, and PCR was performed by a reaction of 30 cycles of a first step at 95° C. for 30 seconds, a second step at 50° C. for 30 seconds, and a third step at 72° C. for 90 seconds, followed by heat treatment at 72° C. for 7 minutes. The obtained PCR product was designated as V192p1.

TABLE 1

| Composition | Volume |
|---|---|
| Template DNA | 2 μL |
| 10 μM Forward primer | 1 μL |
| 10 μM Reverse primer | 1 μL |
| 5 × PrimeSTAR ® buffer (manufactured by Takara Bio) | 4 μL |
| 2.5 mM dNTPs | 2 μL |
| 2.5 U/μL PrimeSTAR ® HS (manufactured by Takara Bio) | 0.5 μL |
| H$_2$O | up to 20 μL |

(2) A reaction solution having the composition in Table 1 was prepared using plasmid pET-FcR9 (disclosed in WO2015/199154) including the polynucleotide (SEQ ID NO: 6) encoding FcR9 (SEQ ID NO: 5) produced by the method disclosed in WO2015/199154 as a template and oligoprimers consisting of the sequences set forth in SEQ ID NO: 3 (5'-TATGCTAGTTATTGCTCAG-3') and SEQ ID NO: 8 (5'-CCTGCCGTGGGCTGNNKGGCAGCAAAAATG-3'). Subsequently, the reaction solution was heat-treated at 95° C. for 2 minutes, and PCR was performed by a reaction of 30 cycles of a first step at 95° C. for 30 seconds, a second step at 50° C. for 30 seconds, and a third step at 72° C. for 90 seconds, followed by heat treatment at 72° C. for 7 minutes. The obtained PCR product was designated as V192p2.

(3) The two types of PCR products (V192p1, V192p2) obtained in (1) and (2) were mixed, thereby preparing a reaction solution having the composition in Table 2. The reaction solution was heat-treated at 98° C. for 5 minutes, and PCR was performed by a reaction of 5 cycles of a first step at 98° C. for 10 seconds, a second step at 55° C. for 5 seconds, and a third step at 72° C. for 1 minute, thereby obtaining a PCR product V192p in which V192p1 and V192p2 were joined to each other.

TABLE 2

| Composition | Concentration/Volume |
| --- | --- |
| PCR product | 2 μL each |
| 2.5 U/μL PrimeSTAR ® HS (manufactured by Takara Bio) | 0.5 μL |
| 5 × PrimeSTAR ® buffer (manufactured by Takara Bio) | 4 μL |
| 2.5 mM dNTPs | 2 μL |
| H₂O | up to 20 μL |

(4) PCR was performed using the PCR product V192p obtained in (3) as a template and oligonucleotides consisting of the sequences set forth in SEQ ID NOs: 2 and 3 as PCR primers. A reaction solution having the composition in Table 3 was prepared. Subsequently, the reaction solution was heat-treated at 98° C. for 5 minutes, and a reaction of 30 cycles of a first step at 98° C. for 10 seconds, a second step at 55° C. for 5 seconds, and a third step at 72° C. for 1 minute was performed. Accordingly, a polynucleotide encoding an Fc-binding protein having a substitution of an amino acid at position 192 in the Fc-binding protein (FcR9) by an optional amino acid was obtained. The obtained polynucleotide was designated as V192p3.

TABLE 3

| Composition | Volume |
| --- | --- |
| PCR product | 2 μL |
| 10 μM Forward primer | 2 μL |
| 10 μM Reverse primer | 2 μL |
| 5 × PrimeSTAR ® buffer (manufactured by Takara Bio) | 10 μL |
| 2.5 mM dNTPs | 4 μL |
| 2.5 U/μL PrimeSTAR ® HS (manufactured by Takara Bio) | 1 μL |
| H₂O | up to 50 μL |

(5) The polynucleotide obtained in (4) was purified, digested with restriction enzymes NcoI and HindIII, and ligated to an expression vector pETMalE (Japanese Unexamined Patent Publication (Kokai) No. 2011-206046) which was preliminarily digested with restriction enzymes NcoI and HindIII, and the resulting product was used for transforming E. coli strain BL21 (DE3).

(6) The obtained transformant was cultured in an LB medium supplemented with 50 μg/mL kanamycin. Plasmids were extracted from the collected bacterial cells (transformants).

(7) Regarding the polynucleotide encoding the Fc-binding protein and its surrounding region in each obtained plasmid, a cycle sequence reaction was performed using a BigDye Terminator v3.1 Cycle Sequencing Kit (manufactured by Life Technologies Corporation) based on the chain terminator method, and the nucleotide sequence was analyzed by a fully automated DNA sequencer (Applied Biosystems 3130 Genetic Analyzer (manufactured by Life Technologies Corporation)). An oligonucleotide consisting of the sequence set forth in SEQ ID NO: 2 or SEQ ID NO: 3 was used as a sequencing primer upon the analysis. As a result of sequence analysis, transformants expressing Fc-binding proteins each having a substitution of Val at position 192 (position 176 of SEQ ID NO: 1) in the Fc-binding protein FcR9 (SEQ ID NO: 5) by one of Ala, Arg, Asn, Asp, Cys, Gln, Glu, Gly, His, Ile, Leu, Lys, Met, Phe, Pro, Ser, Thr, Trp, and Tyr were obtained.

Example 2 Evaluation of IgG1-Binding Ability of Fc-Binding Protein (1) The each transformant expressing Fc-binding protein produced in Example 1 was inoculated in a 20 mL of a 2YT liquid medium supplemented with 50 μg/mL kanamycin and aerobically cultured with shaking overnight at 37° C., thereby performing preculture, respectively.

(2) Each preculture solution in a volume of 10 mL was inoculated in 1000 mL of a 2YT liquid medium (peptone at 16 g/L, yeast extract at 10 g/L, sodium chloride at 5 g/L) supplemented with 50 μg/mL kanamycin and aerobically cultured with shaking at 37° C.

(3) The culture temperature was changed to 20° C. 1.5 hours after the start of culture, followed by shaking culture for 30 minutes. Thereafter, isopropyl-β-thiogalactopyranoside (IPTG) was added to yield a final concentration of 0.01 mM, and shaking culture was continued aerobically overnight at 20° C.

(4) After the end of culture, cells were collected by centrifugation, suspended in a buffer (20 mM Tris-HCL buffer containing 150 mM NaCl (pH 7.4)), and ultrasonically disrupted. Thereafter, the supernatant was collected by centrifugation.

(5) The collected supernatant was allowed to pass through a column filled with Ni Sepharose® 6 Fast Flow (manufactured by GE Healthcare) and washed with a sufficient amount of a washing buffer (20 mM Tris-HCL buffer containing 150 mM NaCl (pH 7.4)), followed by elution with an elution buffer (20 mM Tris-HCl buffer containing 150 mM NaCl and 500 mM imidazole (pH 7.4)). Then, the elution fraction was collected.

(6) The elution fraction collected in (5) was allowed to pass through a column filled with IgG Sepharose® 6 Fast Flow (manufactured by GE Healthcare) and washed with a sufficient amount of a washing buffer (20 mM Tris-HCl buffer containing 150 mM NaCl (pH 7.4)), followed by elution with an elution buffer (100 mM glycine buffer (pH 3.0)). Then, the elution fraction was collected.

(7) IgG1-binding ability of each Fc-binding protein collected as the elution fraction in (6) was evaluated using the surface plasmon resonance method. Upon measurement of the binding ability using the surface plasmon resonance method, Biacore™ T100 (manufactured by GE Healthcare) was used as a measurement system, Sensor Chip CM5 (manufactured by GE Healthcare) was used as a sensor chip, and Biacore™ T100 Evaluation Software (manufactured by GE Healthcare) was used as analysis software.

(8) A solution prepared by diluting IgG1 (manufactured by Sigma-Aldrich) with HBS-EP (manufactured by GE Healthcare) was supplied to a sensor chip on which each Fc-binding protein was separately immobilized using an Amine Coupling Kit (manufactured by GE Healthcare), thereby obtaining a sensorgram. Curve fitting was performed based on the sensorgram so as to calculate IgG1-binding ability.

Here, it is generally known that when affinity between an Fc-binding protein and an antibody decreases, the ability of the Fc-binding protein to retain the antibody is weakened, and the capacity for adsorption is reduced. Meanwhile, in a column filled with an insoluble carrier (resin) having an Fc-binding protein immobilized thereon, when binding ability between the Fc-binding protein and an antibody is reduced, ability to retain the antibody when adding the antibody for elution is weakened. This allows elution while the binding force is lowered, thereby facilitating separation. As a result of calculation of affinity to the IgG1 antibody by the above-described method, it was found that among the produced Fc-binding proteins, a protein having an amino acid substitution of Val at position 192 of SEQ ID NO: 5 (corresponding to position 176 of SEQ ID NO: 1) by Phe (hereinafter referred to as "FcR9_F") has lower antibody affinity than FcR9 (SEQ ID NO: 5) serving as a reference.

The amino acid sequence of FcR9_F to which a signal sequence and a polyhistidine tag were added is set forth in SEQ ID NO: 9, and the polynucleotide sequence encoding the FcR9_F is set forth in SEQ ID NO: 10. In SEQ ID NO: 9, a MalE signal peptide ranges from methionine (Met) at position 1 to alanine (Ala) at position 26, a linker sequence ranges from lysine (Lys) at position 27 to methionine (Met) at position 32, the amino acid sequence of FcR9_F (corresponding to a region from position 17 to position 192 of SEQ ID NO: 1) ranges from glycine at position 33 (Gly) to glutamine at position 208 (Gln), a linker sequence ranges from glycine (Gly) at position 209 to glycine (Gly) at position 210, and a tag sequence ranges from histidine (His) at position 211 to histidine (His) at position 216. In addition, phenylalanine of Val192Phe is located at position 192 of SEQ ID NO: 9.

Table 4 lists the results of calculating affinity to IgG1. In Table 4, the lower the KD value (dissociation constant) means the higher the affinity. It is understood that FcR9_F (SEQ ID NO: 9), which is an Fc-binding protein having an amino acid substitution of Val192Phe, has a higher dissociation constant, i.e., lower affinity to an antibody, compared to FcR9 (SEQ ID NO: 5) lacking the substitution. Accordingly, it is suggested that when an antibody is separated by a method including a step of adding a solution containing an antibody to a column filled with an insoluble carrier having the Fc-binding protein immobilized thereon so as to allow the carrier to adsorb the antibody and a step of eluting the antibody adsorbed by the carrier using an elution solution, the antibody can be separated with a high degree of separation and high efficiency using, as the Fc-binding protein, a protein having at least an amino acid substitution of Val192Phe in the Fc-binding protein FcR9 (SEQ ID NO: 5) disclosed in WO2015/199154 because affinity to the antibody is lowered as compared to when using FcR9.

TABLE 4

| Fc-binding protein | | Association rate constant ka [1/Ms] | Dissociation rate constant kd [1/s] | Dissociation constant $K_D$ [M] |
|---|---|---|---|---|
| Name | Substitution position | | | |
| FcR9 | (Reference) | $4.05 \times 10^5$ | $3.13 \times 10^{-2}$ | $7.73 \times 10^{-8}$ |
| FcR9_F | Val192Phe | $9.02 \times 10^4$ | $3.01 \times 10^{-1}$ | $3.28 \times 10^{-6}$ |

Example 3 Production of Fc-Binding Protein of Invention (FcR9_F_Cys) Having Cysteine Tag Added (1) PCR was performed using an expression vector pET-FcR9_F including the polynucleotide set forth in SEQ ID NO: 10 encoding a protein consisting of the amino acid sequence set forth in SEQ ID NO: 9 produced in Example 2 as a template. Primers used in the PCR were oligonucleotides consisting of the sequences set forth in SEQ ID NO: 11 (5'-TAGCCATGGGCATGCGTACCGAA-GATCTGCCGAAAGC-3') and SEQ ID NO: 12 (5'-CC-CAAGCT-TATCCGCAGGTATCGTTGCGGCACCCTTGGGTAATG GTAATATTCACGG TCTCGCTGC-3'). A reaction solution having the composition in Table 3 was prepared. Subsequently, the reaction solution was heat-treated at 98° C. for 5 minutes, and PCR was performed by a reaction of 30 cycles of a first step at 98° C. for 10 seconds, a second step at 55° C. for 5 seconds, and a third step at 72° C. for 1 minute.

(2) The polynucleotide obtained in (1) was purified and digested with restriction enzymes NcoI and HindIII, and ligated to an expression vector pTrc-PelBV3 produced by the method disclosed in WO2015/199154, which was preliminarily digested with restriction enzymes NcoI and HindIII. E. coli strain W3110 was transformed using the ligation product.

(3) After the obtained transformant was cultured in an LB medium containing 100 µg/mL carbenicillin, an expression vector pTrc-FcR9_F_Cys was obtained using a QIAprep Spin Miniprep kit (manufactured by QIAGEN).

(4) The nucleotide sequence of pTrc-FcR9_F_Cys was analyzed in the same manner as in Example 1 (7) except that an oligonucleotide consisting of the sequence set forth in SEQ ID NO: 13 (5'-TGTGGTATGGCTGTGCAGG-3') or SEQ ID NO: 14 (5'-TCGGCATGGGGTCAGGTG-3') was used as a sequencing primer.

The amino acid sequence of a polypeptide expressed in the vector pTrc-FcR9_F_Cys is set forth in SEQ ID NO: 15, and the sequence of a polynucleotide encoding the polypeptide is set forth in SEQ ID NO: 16. In SEQ ID NO: 15, an improved PelB signal peptide ranges from methionine (Met) at position 1 to alanine (Ala) at position 22, the amino acid sequence of the Fc-binding protein FcR9_F (corresponding to a region from position 33 to position 208 of SEQ ID NO: 9) ranges from glycine (Gly) at position 24 to glutamine (Gln) at position 199, and a cysteine tag sequence ranges from glycine (Gly) at position 200 to glycine (Gly) at position 207.

Example 4 Preparation of FcR9_F_Cys (1) The transformant expressing FcR9_F_Cys produced in Example 3 was inoculated in 400 mL of a 2YT liquid medium (peptone at 16 g/L, yeast extract at 10 g/L, sodium chloride at 5 g/L) containing 100 µg/mL carbenicillin in a 2-L baffled flask and aerobically cultured with shaking overnight at 37° C., thereby performing preculture.

(2) The culture solution of (1) in a volume of 180 mL was inoculated in 1.8 L of a liquid medium containing glucose at 10 g/L, yeast extract at 20 g/L, phosphate trisodium dodecahydrate at 3 g/L, hydrogen phosphate disodium dodecahydrate at 9 g/L, ammonium chloride at 1 g/L, and carbenicillin at 100 mg/L, and main culture was performed using a 3-L fermenter (manufactured by Biott Corporation). Main culture was initiated under conditions set as follows: 30° C., pH 6.9 to 7.1, an airflow rate of 1 VVM, and a saturated dissolved oxygen concentration of 30%. For pH control, 50% phosphoric acid was used as an acid, and 14% ammonia water was used as an alkali, dissolved oxygen was controlled by changing the stirring rate, and the lower and upper limits of the number of rotations of stirring were set to 500 rpm and 1000 rpm, respectively. At a time point when the glucose concentration became unmeasurable after the start of culture, a feed medium (glucose at 248.9 g/L, yeast extract at 83.3 g/L, magnesium sulfate heptahydrate at 7.2 g/L) was added while controlling dissolved oxygen (DO).

(3) When the 600-nm optical density (OD 600 nm) serving as an indicator of the amount of bacterial cells reached about 150, the culture temperature was decreased to 25° C., and it was confirmed that the temperature reached the preset temperature. Subsequently, IPTG was added to yield a final concentration of 0.5 mM, and culture was continued at 25° C.

(4) Culture was terminated about 48 hours after the start of culture, and the culture solution was centrifuged at 4° C. and 8000 rpm for 20 minutes, thereby collecting bacterial cells.

(5) The collected bacterial cells were suspended in a 20 mM Tris-HCl buffer (pH 7.0) to yield a concentration of 5 mL/1 g (of bacterial cells), and the bacterial cells were disrupted using an ultrasonicator (Insonator 201M (trade name), manufactured by KUBOTA Corporation co., ltd.) at 4° C. and an output power of about 150 W for about 10 minutes. A solution of the disrupted bacterial cells was centrifuged twice at 4° C. and 8000 rpm for 20 minutes, thereby collecting the supernatant.

(6) The supernatant obtained in (5) was applied to VL 32×250 Column (manufactured by MERCK MILLIPORE) filled with 140 mL of TOYOPEARL CM-650M (manufactured by Tosoh Corporation) which was preliminarily equilibrated with a 20 mM phosphate buffer (8 mM sodium dihydrogen phosphate, 12 mM disodium hydrogen phosphate) (pH 7.0) at a flow rate of 5 mL/min. After washing with the buffer used for equilibration, elution was performed using 20 mM phosphate buffer (pH 7.0) containing 0.5 M sodium chloride.

(7) The eluate obtained in (6) was applied to an XK 26/20 Column (manufactured by GE Healthcare) filled with 90 mL of IgG Sepharose® (manufactured by GE Healthcare) which was preliminarily equilibrated with 20 mM Tris-HCl buffer (pH 7.4) containing 150 mM sodium chloride. After washing with the buffer used for equilibration, elution was performed using 0.1 M glycine-HCl buffer (pH 3.0). The pH of the eluate was adjusted to a neutral range with the addition of 1 M Tris-HCl buffer (pH 8.0) in an amount one-fourth the amount of the eluate.

As a result of the purification, about 20 mg of high-purity FcR9_F_Cys was obtained.

Example 5 Preparation of Fc-Binding Protein (FcR9_F)-Immobilized Gel and Antibody Separation (1) After activation of hydroxyl groups on the surface of a hydrophilic vinyl polymer for a separating resin (manufactured by Tosoh Corporation: TOYOPEARL) in a volume of 2 mL with iodoacetyl groups, 4 mg of FcR9_F_Cys prepared in Example 4 was reacted therewith, thereby obtaining FcR9_F-immobilized gel.

(2) A stainless-steel column having a size of φ4.6 mm×75 mm was filled with 1.2 mL of the FcR9_F-immobilized gel prepared in (1), thereby preparing an FcR9_F column.

(3) The FcR9_F column prepared in (2) was connected to a high performance liquid chromatography system (manufactured by Tosoh Corporation) and equilibrated with 20 mM acetate buffer (pH 5.0) containing 50 mM sodium chloride.

(4) Five microliters of a monoclonal antibody (RITUXAN, manufactured by Zenyaku Kogyo Co., Ltd.), which was diluted with phosphate buffered saline (PBS) (pH 7.4) to yield a concentration of 1.0 mg/mL, was added at a flow rate of 0.6 mL/min.

(5) Washing was performed with the equilibration buffer for 2 minutes while the flow rate was maintained at 0.6 mL/min. Subsequently, a monoclonal antibody adsorbed was eluted with a pH gradient of 10 mM glycine-HCl buffer (pH 3.0) (i.e., a gradient in which 10 mM glycine-HCl buffer (pH 3.0) accounts for 100% in 28 minutes).

FIG. 2 depicts the results (elution pattern). The monoclonal antibody was separated into a plurality of peaks, but not a single peak as in the case of gel filtration chromatography, because it interacted with the Fc-binding protein.

(6) Each of Peaks 1 to 3 in the elution pattern depicted in FIG. 2 was separately collected into a container so as to obtain an isolation fraction of each peak.

Comparative Example 1 Preparation of Fc-Binding Protein (FcR9)-Immobilized Gel and Antibody Separation Antibody separation was carried out by preparing Fc-binding protein (FcR9)-immobilized gel in the same manner as in Examples 3 to 5 except that the Fc-binding protein FcR9 (SEQ ID NO: 5) disclosed in WO2015/199154 was used as an Fc-binding protein to be immobilized on an insoluble carrier.

FIG. 3 depicts the results (elution pattern). It is understood that elution peaks are close to each other and the resolution is low, compared to the elution pattern in Example 5 (FIG. 2). In other words, it was found that antibody separation ability is improved with the use of gel having the Fc-binding protein of the present invention having an amino acid substitution of Val192Phe (FcR9_F) immobilized thereon, compared to when using gel having the Fc-binding protein lacking the amino acid substitution (FcR9) immobilized thereon.

Example 6 Examination of Equilibration Buffer

Example 6 was carried out in the same manner as in Example 5 except that the equilibration buffer used in Example 5 (3) was changed to any of the following (a) to (c).
(a) 20 mM acetate buffer containing 50 mM sodium chloride (pH 5.5)
(b) 20 mM acetate buffer containing 50 mM sodium chloride (pH 5.6)
(c) 20 mM MES buffer containing 50 mM sodium chloride (pH 6.0)

Figure 5:
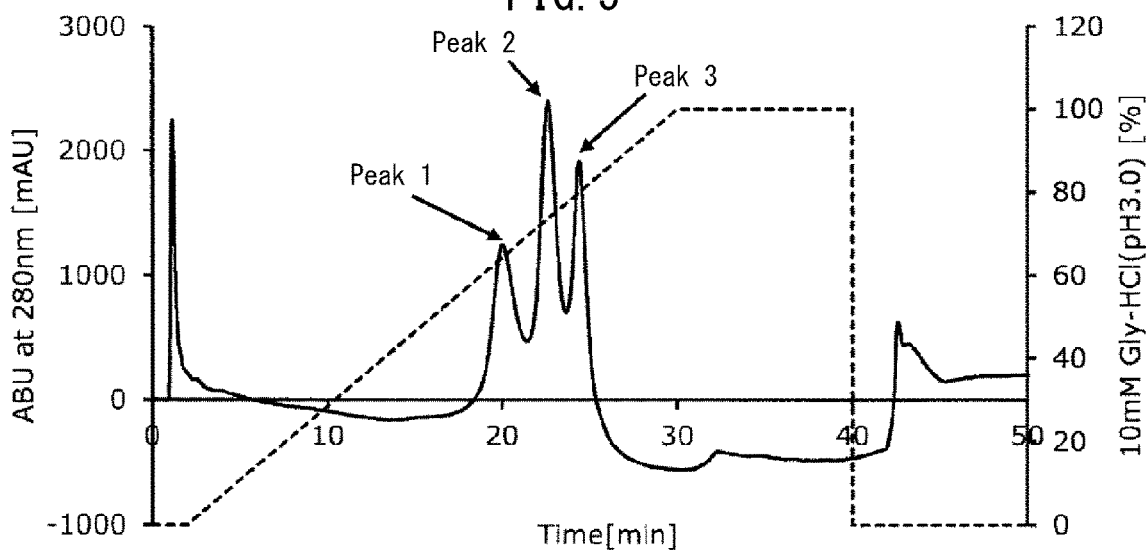
FIG. 5 depicts an elution pattern (chromatogram) when the pH of an equilibration buffer was set to 5.6 in Example 6.
Figure 6:
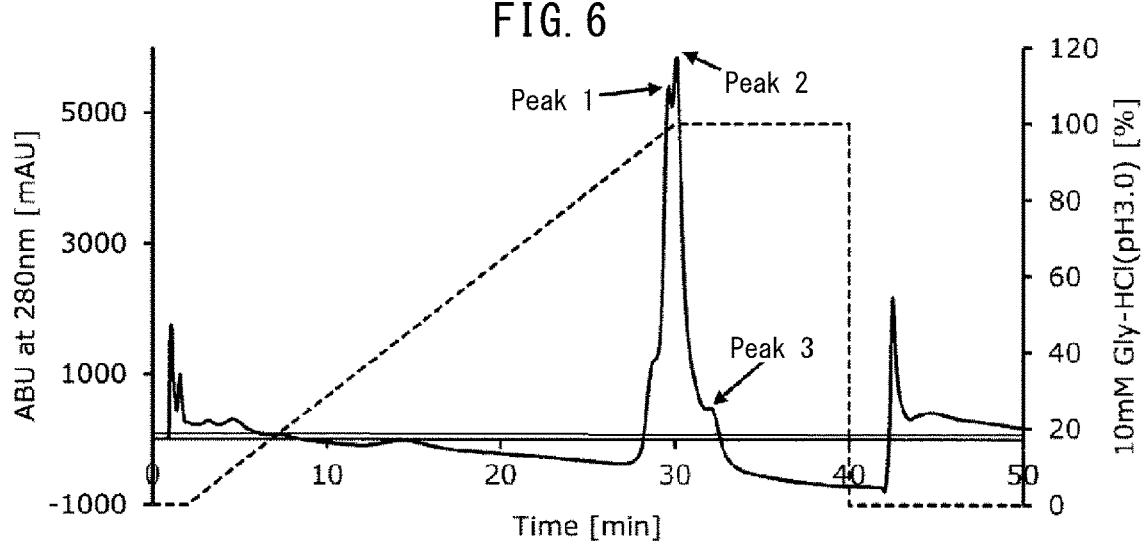
FIG. 6 depicts an elution pattern (chromatogram) when the pH of an equilibration buffer was set to 6.0 in Example 6.

The obtained elution patterns are depicted in FIG. 4 (equilibration buffer (a)), FIG. 5 (equilibration buffer (b)), and FIG. 6 (equilibration buffer (c)). In addition, among the elution patterns obtained in this Example, Example 5 (FIG. 2), and Comparative Example 1 (FIG. 3), peaks corresponding to the monoclonal antibody were designated as Peak 1, Peak 2, and Peak 3 in the ascending order of elution time, and the resolution between Peak 1 and Peak 2 and the resolution between Peak 2 and Peak 3 were calculated using the following formula. Table 5 lists the results.

Resolution (Rs value)=1.18×(Elution time of late elution time peak−Elution time of early elution time peak)/(Half width of early elution time peak+Half width of late elution time peak)

The higher the resolution (Rs value), the better the separation performance.

The inventors previously revealed that antibodies obtained by isolating elution fractions based on the Peak 1, Peak 2, and Peak 3 have different levels of antibody dependent cellular cytotoxicity (ADCC (Japanese Unexamined Patent Publication (Kokai) No. 2016-23152). Therefore, by isolating an antibody using the separation method with high resolution in Example 5, it is possible to separate, for example, antibodies having different levels of ADCC with good accuracy.

TABLE 5

| | Separation condition | | Resolution Rs value | |
|---|---|---|---|---|
| | Fc-binding protein | Equilibration buffer pH | Peaks 1-2 | Peaks 2-3 |
| Example 5 | FcR9_F | 5.0 | 0.95 | 1.10 |
| Comparative Example 1 | FcR9 | 5.0 | 0.85 | 0.74 |
| Example 6 (a) | FcR9_F | 5.5 | 1.22 | 1.11 |
| Example 6 (b) | FcR9_F | 5.6 | 1.18 | 1.13 |
| Example 6 (c) | FcR9_F | 6.0 | 0.05 | 0.09 |

As a result of comparison between the results of Comparative Example 1 (FcR9) and the results of Example 5 (FcR9_F) in Table 5, it is understood that the resolution Rs value and the antibody separation ability are higher in Example 5. In other words, it is also understood from the resolution values obtained by calculation that when using gel having the Fc-binding protein having an amino acid substitution of Val192Phe in FcR9 immobilized thereon, antibody separation ability is improved, compared to when using gel having FcR9 immobilized thereon.

In addition, it is understood from the results of Examples 5 and 6 that when the pH of equilibration buffer was 5.5 or 5.6 (Example 6 of (a) and (b)) rather than 5.0 (Example 5), the resolution (Rs value) increased, while the resolution remarkably decreased at pH 6.0 (Example 6 (c)) indicating that separation was substantially unsuccessful. It can be said from these results that the pH of equilibration buffer is favorably from 4.5 to 5.8, and when the pH is from 5.2 to 5.7, it is preferable in that antibody separation ability is further improved.

Example 7 Measurement of Antibody Dependent Cellular Cytotoxicity (ADCC) of Separated Antibody (1) The regions of Peaks 1 and 3 in the chromatogram depicted in FIG. 2, which were separated in Example 5, were isolated. Isolation was repeated, the buffer was changed to PBS (10 mM disodium hydrogen phosphate, 1.76 mM potassium dihydrogen phosphate, 137 mM sodium chloride, 2.7 mM Potassium chloride) (pH 7.4) while pooled Peaks 1 and 3 were concentrated via an ultrafiltration membrane (manufactured by MERCK MILLIPORE). Thereafter, the concentrations of the monoclonal antibody in Peak 1 and the monoclonal antibody in Peak 3 after concentration and buffer exchange and the concentration of the monoclonal antibody before separation were measured at an absorbance at 280 nm.

(2) ADCC Activity Measurement ADCC activity of the monoclonal antibody included in each peak and that of the monoclonal antibody before separation were measured in accordance with the manual of an ADCC Reporter Bioassay Kit (manufactured by Promega Corporation) by the following method.

(2-1) ADCC assay buffer was prepared by mixing 1.4 mL of Low IgG Serum and 33.6 mL of an RPMI 1640 medium. This ADCC assay buffer was used for creating an eight-step dilution series for each of the monoclonal antibody in Peak 1, the monoclonal antibody in Peak 3, and the monoclonal antibody before separation by three-fold dilution at each step starting from 3 μg/mL.

(2-2) Raji cells were adjusted to have a concentration of about 5×10$^5$ cells/mL with the ADCC assay buffer and added to a 96-well plate (3917: manufactured by Corning Incorporated) at 25 μL/well. The dilution series of each of the monoclonal antibody in Peak 1, the monoclonal antibody in Peak 3, and the monoclonal antibody before separation created in (2-1), and the ADCC assay buffer alone as a blank were separately added to wells containing Raji cells at 25 μL/well.

(2-3) Effector cells (manufactured by Promega Corporation) were adjusted to have a concentration of about 3.0×10$^5$ cells/mL with the ADCC assay buffer and added to wells containing Raji cells and the antibody at 25 μL/well. Thereafter, the 96-well plate was left to stand still in a $CO_2$ incubator (5% $CO_2$, 37° C.) for 6 hours.

(2-4) The 96-well plate was left to stand still at room temperature for 5 to 30 minutes, and then, a Luciferase Assay Reagent (manufactured by Promega Corporation) was added at 75 μL/well. Reaction was caused to proceed at room temperature for 30 minutes, followed by luminescence measurement by a GloMax® Multi Detection System (manufactured by Promega Corporation).

Figure 7:
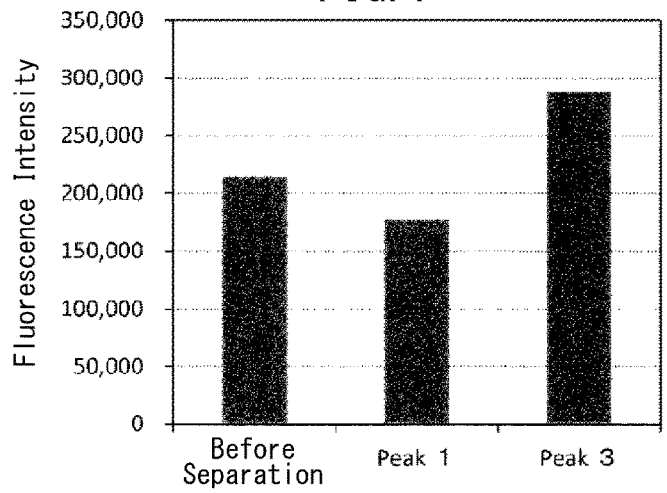
FIG. 7 is a graph indicating the results of measuring ADCC activity of a monoclonal antibody included in the isolated peaks in Example 7.

(3) FIG. 7 depicts the results of comparing the luminescence intensities of the monoclonal antibody of Peak 1 and the monoclonal antibody of Peak 3, each peak being separated in Example 5, and the luminescence intensity of the monoclonal antibody before separation, which were calculated by subtracting the blank luminescence intensity from the measured luminescence intensity. The results indicate that the higher the luminescence intensity, the higher the ADCC activity. Although the ADCC activity of Peak 1 was lower than that before separation, the luminescence intensity of Peak 3 was about 1.5 times higher than before separation. It is understood from the results that the monoclonal antibody contained in Peak 3 has higher ADCC activity than that of the monoclonal antibody before separation and that of the monoclonal antibody contained in Peak 1. Accordingly, it was found that an antibody with higher ADCC activity is the one obtained by late elution from the FcR9_F column prepared in Example 5 (long retention time in the column), and it was confirmed that a monoclonal antibody can be separated based on ADCC activity using the present invention gel.

Example 8 Analysis of Antibody Contained in Culture Solution and Separation Pattern (1)

(1) Construction of Antibody-Producing Cells (1-1) A polynucleotide obtained by adding a polynucleotide (heavy chain signal peptide nucleotide sequence: SEQ ID NO: 27; light chain signal peptide nucleotide sequence: SEQ ID NO: 28) encoding an antibody-derived signal peptide for secretion expression (heavy chain signal peptide amino acid sequence: SEQ ID NO: 25; light chain signal peptide amino acid sequence: SEQ ID NO: 26) to the 5' end of a polynucleotide (rituximab heavy chain nucleotide sequence: SEQ ID NO: 21; rituximab light chain nucleotide sequence: SEQ ID NO: 22; bevacizumab heavy chain nucleotide sequence: SEQ ID NO: 23; bevacizumab light chain nucleotide sequence: SEQ ID NO: 24) encoding rituximab (heavy chain amino acid sequence: SEQ ID NO: 17; light chain amino acid sequence: SEQ ID NO: 18) or bevacizumab (heavy chain amino acid sequence: SEQ ID NO: 19; light chain amino acid sequence: SEQ ID NO: 20) was introduced into a commercially available vector (pCAG-Neo, manufactured by Wako Pure Chemical Industries, Ltd.) by an ordinary method.

(1-2) CHO cells (strain DG44) were transfected using the constructed antibody expression vector by the Lipofectamine method, and antibody-producing cells were obtained by selection using antibiotics.

(1-3) A high-expression strain was selected by single cloning from the group of the obtained antibody-producing cells, thereby establishing high-expression antibody-producing cells.

(2) Culture of Antibody-Producing Cells (2-1) Antibody-producing cells were seeded in an 125 mL Erlenmeyer flask (manufactured by Corning Incorporated) containing 20 mL of CD OptiCHO™ medium (manufactured by Thermo Fisher Scientific) to which a glutamine solution (manufactured by Thermo Fisher Scientific) and antibiotic G418 (manufactured by Thermo Fisher Scientific) were added to yield a concentration of $5\times10^5$ cells/mL so as to perform shaking culture at 37° C. and 125 rpm in the presence of 8% $CO_2$.

(2-2) The viable cell density and cell viability were determined by a commercially available automated cell counter (manufactured by Thermo Fisher Scientific) once every other day.

(2-3) The culture scale was successively expanded by an ordinary method, and eventually, main culture in 1 L of the medium was initiated. The viable cell density and cell viability were determined in the same manner as in (2-2), and culture was continued by adding the medium described in (2-1) as appropriate.

(3) Sampling of Culture Solution and Analysis by FcR9_F Column (3-1) The culture solution was sampled by the number of days of culture and the viable cell density and cell viability were determined. In addition, the sampled culture solution was used for determining the antibody production by the HPLC method using an affinity chromatography column for antibody quantification (TSKgel® Protein A-5PW, manufactured by Tosoh Corporation).

(3-2) The culture solution sampled by the number of days of culture was analyzed using the FcR9_F column prepared in Example 5 by the same method as in Example 6 (b), thereby obtaining a pattern of separation of the antibody contained in the culture solution.

Figure 8:
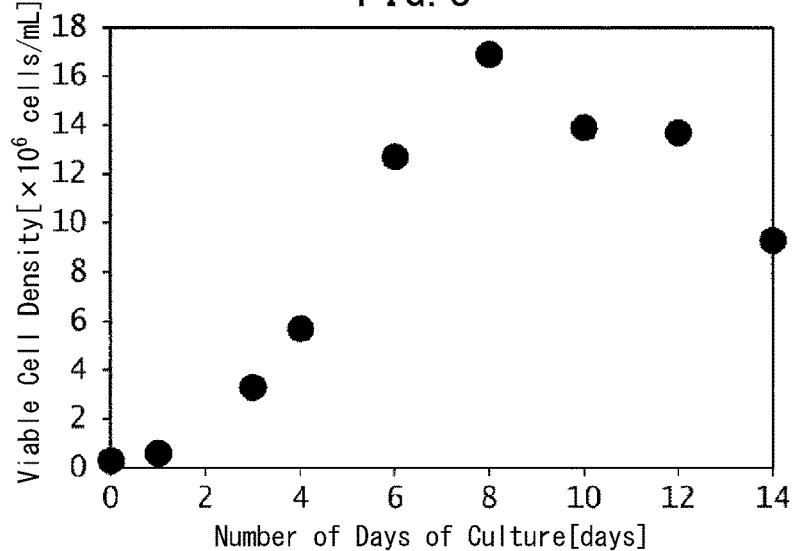
FIG. 8 is a graph indicating temporal changes in the viable cell density by the number of days of culture of antibody-producing cells in Example 8.
Figure 9:
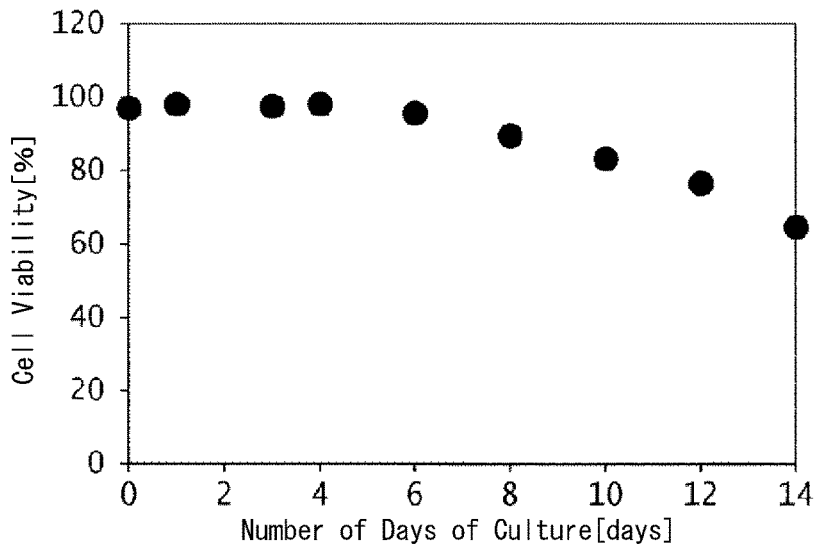
FIG. 9 is a graph indicating temporal changes in the cell viability by the number of days of culture of antibody-producing cells in Example 8.
Figure 10:
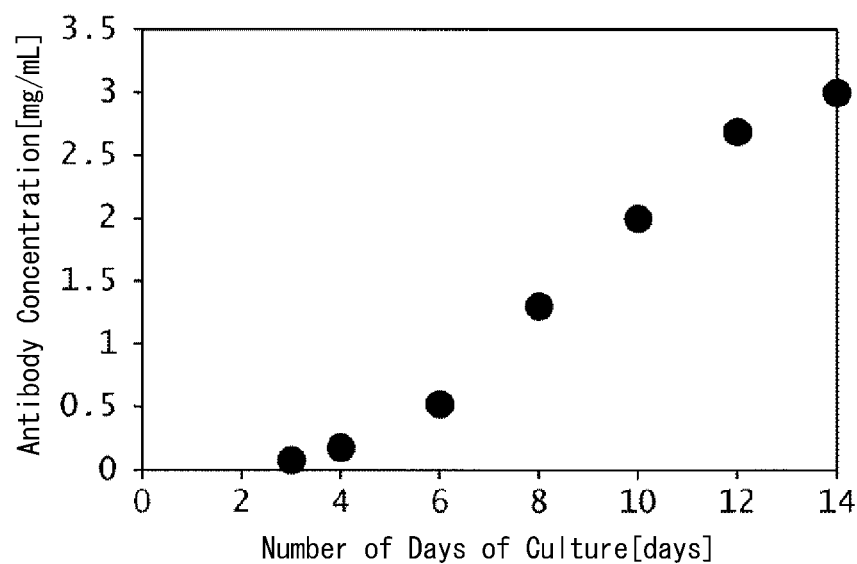
FIG. 10 is a graph indicating temporal changes in the antibody concentration (antibody production) by the number of days of culture of antibody-producing cells in Example 8.
Figure 11:
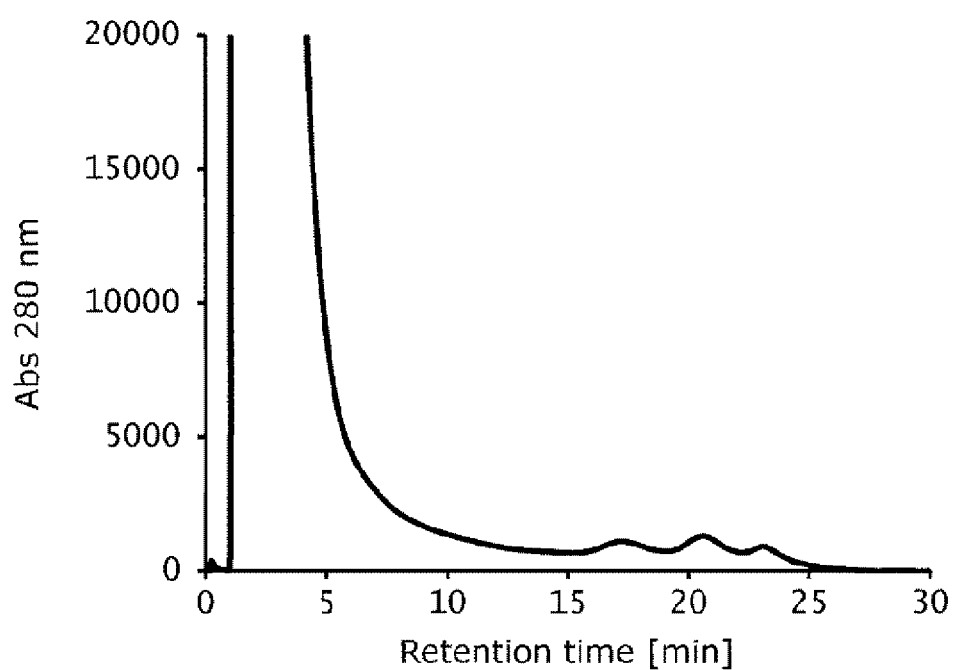
FIG. 11 is a chromatogram indicating the results of analysis of the culture solution containing an antibody using the FcR9_F column in Example 8.
Figure 12:
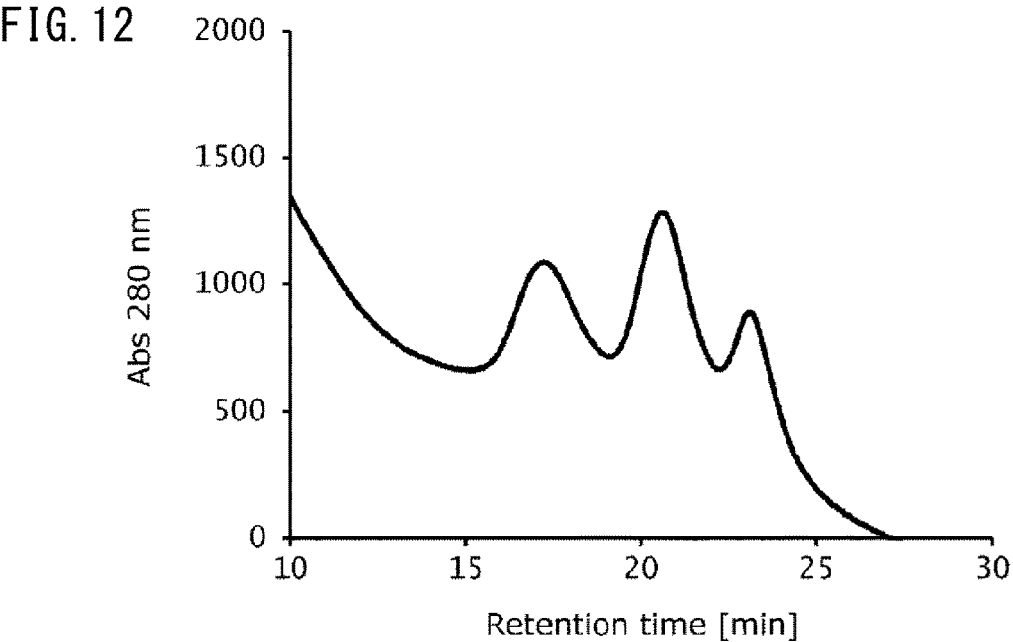
FIG. 12 is an enlarged view of the region between 10 minutes to 30 minutes of elution time (retention time) in the chromatogram in FIG. 11.

FIGS. 8 to 10 depict the results of the viable cell density, cell viability, and antibody concentration (antibody production) obtained by the number of days of culture, respectively. In addition, FIG. 11 depicts the results (chromatogram) obtained by analyzing the culture solution on Day 3 of culture using the FcR9_F column. Contaminants accounting for the majority of the culture solution could be observed as a pass-through fraction at a peak around 1 to 5 minutes of elution time (retention time). Meanwhile, when the region of 10 to 30 minutes of elution time was enlarged (FIG. 12), a plurality of peaks derived from the antibody contained in the culture solution were confirmed. It is understood from the above results that by analyzing an antibody contained in the culture solution during culture using the FcR9_F column of the present invention, it is possible to separate the antibody contained in the culture solution during culture based on its sugar chain structure.

Figure 13:
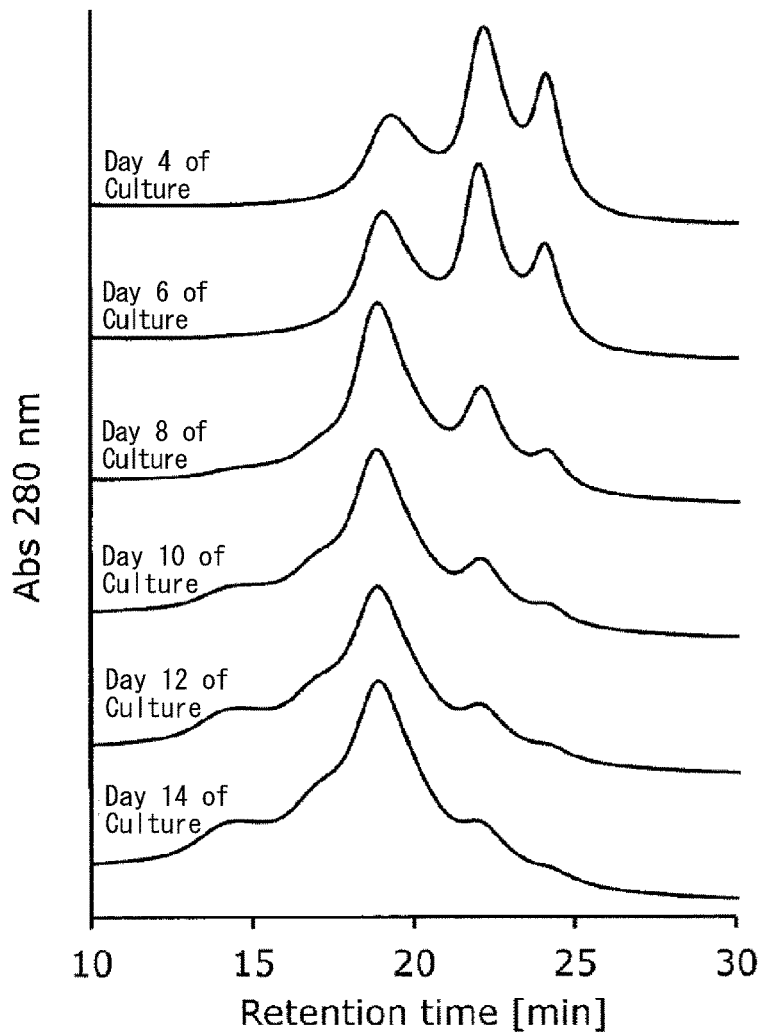
FIG. 13 depicts chromatograms (elution time (retention time): region between 10 minutes to 30 minutes) indicating the results of analysis of the culture solution containing an antibody on different days of culture using the FcR9_F column in Example 8, the chromatograms having different peak forms by the number of days of culture.

Further, the culture solution was analyzed in the same manner using the FcR9_F column on Days 4, 6, 8, 10, 12, and 14 during culture. FIG. 13 is an enlarged view of the region of 10 to 30 minutes of elution time in the analysis results (chromatogram), based on which the peak derived from the antibody can be confirmed. It was possible to recognize differences in the shape and height of a separation peak derived from the sugar chain structure of the antibody with the passage of days during culture and to monitor temporal changes in the sugar chain structure pattern of the antibody from FIG. 13. The above results suggest that step analysis for monitoring culture progress can be readily performed by analyzing the culture solution during culture using the FcR9_F column of the present invention over time. In addition, it is suggested based on the analysis results that examination of culture conditions optimal for production of antibody drugs and prediction of the sugar chain structure of an antibody can be readily carried out.

Example 9 Analysis of Antibody Contained in Culture Solution and Analysis of Separation Pattern (2)

(1) Vectors for expressing the heavy chain of the anti-interleukin 6 receptor (hereinafter "IL-6R") antibody consisting of the amino acid sequence set forth in SEQ ID NO: 29 and the light chain of the anti-IL-6R antibody consisting of the amino acid sequence set forth in SEQ ID NO: 30 were constructed by the method described below.

(1-1) Total synthesis was carried out by adding the restriction enzyme SacII recognition sequence (CCGCGG) to both the 5' end and the 3' end of the gene encoding dihydrofolate reductase (dhfr) and SV40 PolyA set forth in SEQ ID NO: 31 (consigned to Integrated DNA Technologies, Inc.), and the synthesized product was cloned into a plasmid.

(1-2) *E. coli* strain JM 109 was transformed by the plasmid prepared in (1-1). The obtained transformant was cultured, and plasmids were extracted therefrom and digested with restriction enzyme SacII, thereby preparing a gene encoding dhfr-SV40 PolyA. The gene was named dhfr-SV40 PolyA-P1.

(1-3) PCR was performed using a pIRES vector (manufactured by Clontech Laboratories, Inc.) as a template and oligonucleotide primers consisting of the sequences set forth in SEQ ID NO: 32 (5'-TCCCCGCGGGCGGGACTCTGGGGTTCGAAATGAC CG-3') and SEQ ID NO: 33 (5'-TCCCCGCGGGGTGGCTCTAGCCTTAAGTTCGA-GACTG-3'). Specifically, a reaction solution having the composition in Table 6 was prepared. The reaction solution was heat-treated at 98° C. for 30 seconds, and PCR was performed by a reaction of 25 cycles of a first step at 98° C. for 10 seconds, a second step at 55° C. for 5 seconds, and a third step at 72° C. for 5 minutes. As a result of PCR, a region in the pIRES vector, from which the neomycin-resistant gene was removed, was amplified.

TABLE 6

| Composition | Volume |
| --- | --- |
| 10 ng/μL Template DNA | 2 μL |
| 10 μM Forward primer (SEQ ID NO: 32 or 34) | 2 μL |
| 10 μM Reverse primer (SEQ ID NO: 33 or 35) | 2 μL |
| 5 × PrimeSTAR ® buffer (manufactured by Takara Bio) | 10 μL |
| 2.5 mM dNTPs | 4 μL |
| 2.5 U/μL PrimeSTAR ® HS (manufactured by Takara Bio) | 0.5 μL |
| H₂O | up to 50 μL |

(1-4) The PCR product produced in (1-3) was purified, digested with restriction enzyme SacII, and ligated to dhfr-SV40 PolyA-P1 prepared in (1-2). *E. coli* strain JM109 was transformed with the ligation product, and plasmids were extracted from the cultured transformant, thereby obtaining the expression vector pIRES-dhfr including the dhfr gene.

(2) PCR was performed using pIRES-dhfr prepared in (1) as a template and oligonucleotide primers consisting of the sequences set forth in SEQ ID NO: 34 (5'-ACGCGTCGACACTAGAAGCTTTATTGCGGTAGTT-TATCAC-3') and SEQ ID NO: 35 (5'-ACGCGTCGACA-GATCTGTCGAGCCATGTGAGCAAAAGGCC-3'). Specifically, a reaction solution having the composition in Table 6 was prepared. The reaction solution was heat-treated at 98° C. for 5 minutes, and PCR was performed by a reaction of 30 cycles of a first step at 98° C. for 10 seconds, a second step at 55° C. for 5 seconds, and a third step at 72° C. for 7 minutes. As a result of PCR, a region in the pIRES-dhfr vector, from which the CMV promoter gene was removed, was amplified, and designated as pIRES-dhfr-P2.

(3) PCR was performed using pIRES-dhfr-P2 prepared in (2) as a template and oligonucleotide primers consisting of the sequences set forth in SEQ ID NO: 36 (5'-TT-TAAATCAGCGGCCGCGCAGCACCATGGCCT-GAAATAACCTCTG-3') and SEQ ID NO: 37 (5'-ACGGGCACCGGAGCGATCGTTTACCACATTTGTAG AGGTTTTACTTGC-3'). Specifically, a reaction solution having the composition in Table 7 was prepared. The reaction solution was heat-treated at 98° C. for 1 minute, and PCR was performed by a reaction of 30 cycles of a first step at 98° C. for 10 seconds, a second step at 55° C. for 5 seconds, and a third step at 72° C. for 1 minute. The PCR product (i.e., a region including the SV40 promoter, dhfr, and SV40 PolyA) amplified as a result of PCR was designated as dhfr-P3 (SEQ ID NO: 38).

TABLE 7

| Composition | Volume |
| --- | --- |
| 50 ng/µLTemplate DNA | 1 µL |
| 10 µM Forward primer (SEQ ID NO: 36) | 2 µL |
| 10 µM Reverse primer (SEQ ID NO: 37) | 2 µL |
| 5 × PrimeSTAR ® buffer (manufactured by Takara Bio) | 10 µL |
| 2.5 mM dNTPs | 4 µL |
| 2.5 U/µL PrimeSTAR ® HS (manufactured by Takara Bio) | 0.5 µL |
| H$_2$O | up to 50 µL |

(4) pFUSEss-CHIg-hG1 including a human antibody heavy chain constant region (manufactured by InvivoGen) and dhfr-P3 prepared in (3) were digested with restriction enzymes NotI and PvuI, purified, and ligated to each other. E. coli strain JM109 was transformed with the ligation product, and plasmids were extracted from the cultured transformant, thereby obtaining pFUSEss-CHIg-hG1 including the SV40 promoter, dhfr, and SV40 PolyA. The plasmid in which the SV40 promoter, dhfr, and SV40 PolyA were incorporated into pFUSEss-CHIg-hG1 was designated as pFU-CHIg-dhfr.

(5) Total synthesis of a polynucleotide encoding the anti-IL-6R antibody heavy chain variable region consisting of the amino acid sequence set forth in SEQ ID NO: 39 with a polynucleotide (SEQ ID NO: 40) to which restriction enzymes EcoRI (GAATTC) and NheI recognition sequence (GCTAGC) were added was conducted (consigned to FASMAC). The synthesized product was cloned into plasmids, and each plasmid was used for transforming E. coli strain JM109. Each obtained transformant was cultured, and plasmids were extracted, digested with restriction enzymes EcoRI and NheI and purified, thereby obtaining a gene encoding the anti-IL-6R antibody heavy chain including a signal peptide. The gene was designated as aIL6RH-P4.

(6) pFU-CHIg-dhfr prepared in (4) was digested with restriction enzymes EcoRI and NheI and purified. The resulting product was ligated to aIL6RH-P4 prepared in (5), and E. coli JM109 was transformed with the ligation product. Plasmids were extracted from the culture solution of the transformant, thereby obtaining an expression vector pFU-aIL6RH for expressing the anti-IL-6R antibody heavy chain.

(7) pFUSE2ss-CLIg-hk including a human antibody light chain constant region (manufactured by InvivoGen) and dhfr-P3 prepared in (3) were separately digested with restriction enzymes NotI and PvuI, purified, and ligated to each other. E. coli strain JM109 was transformed with the ligation product, and plasmids were extracted from the cultured transformant, thereby obtaining pFUSE2ss-CLIg-hk including the SV40 promoter, dhfr, and SV40 PolyA. The plasmid in which the SV40 promoter, dhfr, and SV40 PolyA were incorporated into pFUSE2ss-CLIg-hk was designated as pFU-CLIg-dhfr.

(8) Total synthesis of a polynucleotide encoding the anti-IL-6R antibody light chain variable region consisting of the amino acid sequence set forth in SEQ ID NO: 41 with a polynucleotide (SEQ ID NO: 42) to which restriction enzyme EcoRI (GAATTC) and a BsiWI recognition sequence (CGTACG) were added was conducted (consigned to FASMAC). The synthesized product was cloned into plasmids, and the plasmids were used for transforming E. coli strain JM109. Each obtained transformant was cultured, plasmids were extracted and digested with restriction enzymes EcoRI and BsiWI and purified, thereby obtaining a gene encoding the anti-IL-6R antibody light chain including a signal peptide. The gene was designated as aIL6RL-P5.

(9) pFU-CLIg-dhfr prepared in (7) was digested with restriction enzymes EcoRI and BsiWI and purified. The resulting product was ligated to aIL6RL-P5 prepared in (8), and E. coli JM109 was transformed with the ligation product. Plasmids were extracted from the culture solution of the transformant, thereby obtaining an expression vector pFU-aIL6RL for expressing the anti-IL-6R antibody light chain.

(10) PFU-aIL6RH prepared in (6) and pFU-aIL6RL prepared in (9) were transfected into CHO cells (strain DG44) using Neon Transfection System (manufactured by Thermo Fisher Scientific). Thereafter, transformed cells were cultured on CD OptiCHO™ Medium (Thermo Fisher Scientific) and gene amplification was performed using 50 ng/mL methotrexate (MTX).

(11) Single cloning was performed by the limiting dilution method, and highly productive cells capable of stably producing an anti-IL-6R antibody were selected by ELISA (Enzyme-Linked Immunosorbent Assay) as described below.

(11-1) Soluble human IL-6R (manufactured by Wako Pure Chemical Industries, Ltd.) or anti-human Fab antibody (manufactured by Bethyl Laboratories) was immobilized at 1 µg/well in wells of a 96-well microplate (overnight at 4° C.). After the end of immobilization, blocking was performed with 20 mM Tris-HCl buffer (pH 7.4) containing 2% (w/v) of SKIM MILK (Becton, Dickinson and Company) and 150 mM sodium chloride.

(11-2) After washing with washing buffer (20 mM Tris-HCl buffer (pH 7.4) containing 0.05% [w/v] Tween® 20 and 150 mM NaCl), the culture supernatant containing the antibody was added so that the antibody was allowed to react with the immobilized protein (1 hour at 30° C.).

(11-3) After the end of the reaction, the reaction product was washed with the washing buffer, and a peroxidaselabeled anti-human Fc antibody (manufactured by Bethyl Laboratories) diluted to 100 ng/mL was added at 100 μL/well.

(11-4) After the reaction at 30° C. for 1 hour, the reaction product was washed with the washing buffer, and TMB Peroxidase Substrate (manufactured by KPL) was added at 50 μL/well. Thereafter, color development was stopped by adding 1M phosphoric acid at 50 μL/well. The absorbance at 450 nm was measured using a microplate reader (manufactured by Tecan Group Ltd.), and a highly productive cell line capable of producing an anti-IL-6R antibody was selected.

(12) A highly productive cell line capable of producing an anti-IL-6R antibody was obtained by repeatedly selecting clones by ELISA described in (11) by limiting dilution while increasing the MTX concentration in a stepwise manner until the MTX concentration reached 64 μg/mL.

(13) The cell line obtained in (12) was scaled-up in a stepwise manner and cultured with shaking using 100 mL of CD OptiCHO™ Medium containing 50 μg/mL kanamycin and two 500-mL Erlenmeyer flasks in a $CO_2$ incubator (37° C., 8% $CO_2$). Thereafter, the cell line was inoculated in a jar fermenter (manufactured by Biott Corporation), and CD OptiCHO™ Medium containing 50 μg/mL kanamycin was added to yield a final volume of 1 L. Culture was performed at 80 rpm, pH 7.0, 37° C., and 5% $CO_2$. The $CO_2$ concentration was changed from 5% to 8% on Day 1 of culture, and the stirring speed was changed from 80 rpm to 100 rpm on Day 5 of culture. Culture was continued for 9 days. The culture solution was collected in a volume of 80 mL on Days 3, 5, 7, and 9 of culture.

(14) Cells and impurities were removed from each culture solution obtained in (13). The obtained supernatant was applied to 0.5 mL of TOYOPEARL rProtein A HC-650F (manufactured by Tosoh Corporation) filling an open column which was preliminarily equilibrated with 20 mM Tris-HCl (pH 7.4) containing 150 mM sodium chloride. The column was washed with the buffer used for the equilibration, followed by elution with 4 mL of 100 mM glycine-HCl buffer (pH 3.0). The pH of the elution solution was adjusted to a neutral range with the addition of 1 mL of 1M Tris-HCl (pH 8.0), and the buffer was exchanged to 50 mM citrate buffer (pH 6.5) via an ultrafiltration membrane, thereby obtaining a high-purity soluble anti-IL-6R antibody on Days 3, 5, 7, and 9 of culture.

(15) The purified anti-IL-6R antibodies obtained in (14) were analyzed by the method described below using the FcR9_F column prepared in Example 5 (2).

(15-1) The FcR9_F column prepared in Example 5 (2) was connected to a high performance liquid chromatography system (manufactured by Tosoh Corporation), and equilibration was performed with an equilibration buffer of 50 mM citrate buffer (pH 6.5) at a flow rate of 1.0 mL/min.

(15-2) The purified antibody obtained in (5) diluted with the 1.0 mg/mL equilibration buffer was added in a volume of 5 μL at a flow rate of 1.0 m L/m in.

(15-3) Washing with the equilibration buffer was performed for 2 minutes while maintaining the flow rate at 1.0 mL/min, and then, the antibody adsorbed with a pH gradient of 50 mM citrate buffer (pH 4.5) (i.e., a gradient in which 50 mM citrate buffer (pH 4.5) accounts for 100% in 18 minutes) was eluted.

(16) Structural analysis of the sugar chain of the purified anti-IL-6R antibody obtained in (14) was conducted by a method as described in Japanese Unexamined Patent Publication (Kokai) No. 2016-169197.

Figure 14:
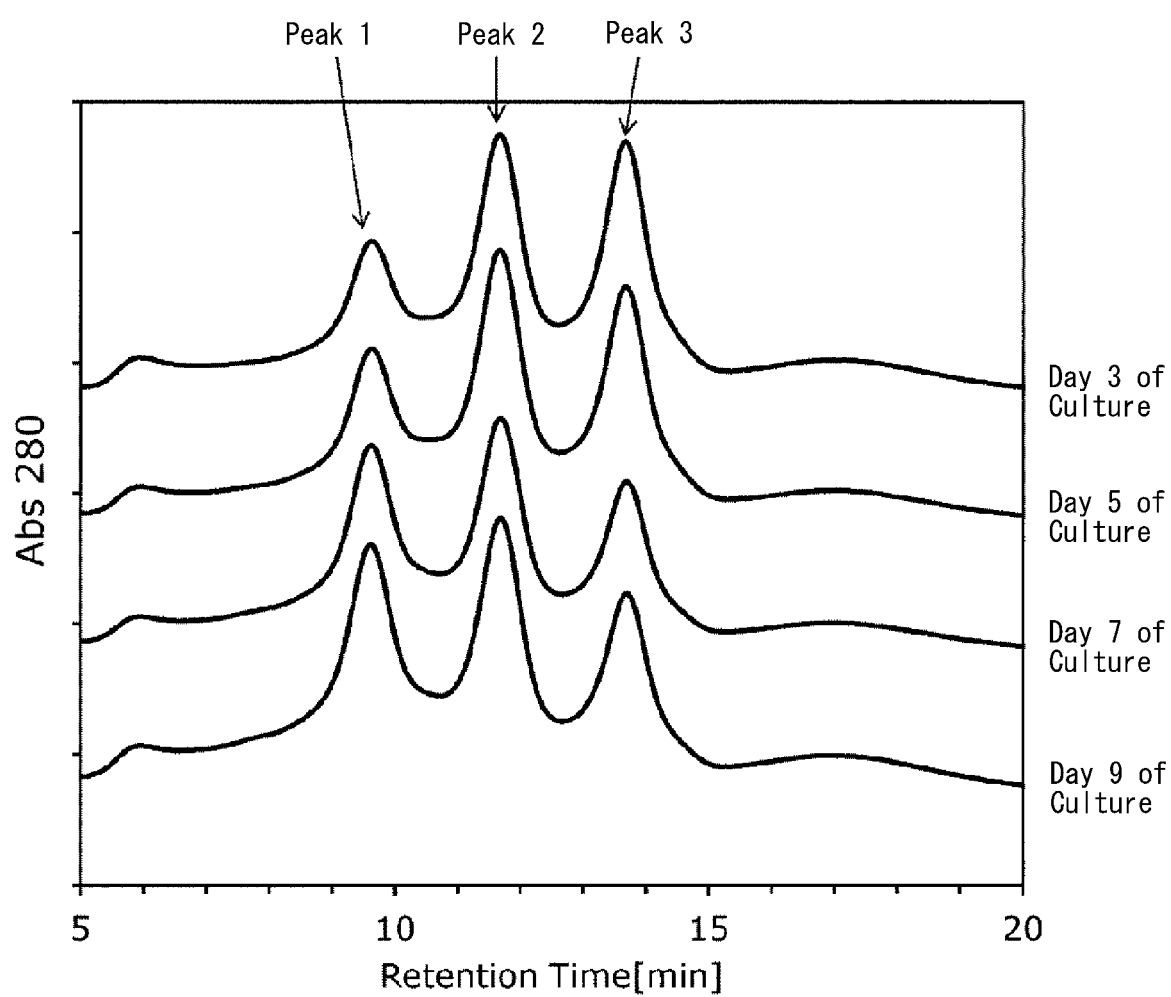
FIG. 14 depicts chromatograms (elution time (retention time): region between 5 minutes to 20 minutes) indicating the results of analysis of an antibody obtained from the culture solution on different days of culture using the FcR9_F column in Example 9, the chromatograms having different peak forms by the number of days of culture.
Figure 15:
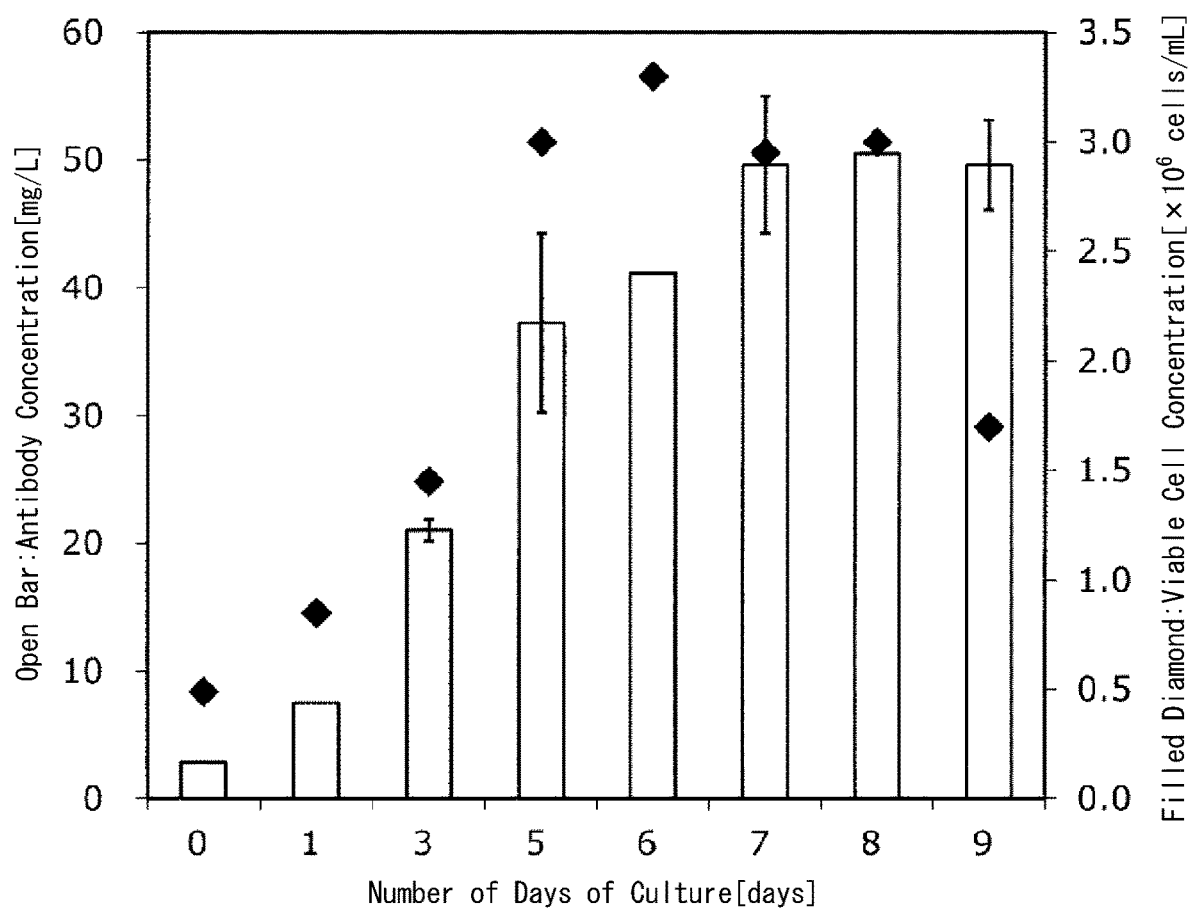
FIG. 15 is a graph indicating temporal changes in the antibody concentration (open bar) and viable cell concentration (filled diamond) by the number of days of culture of the antibody-producing cells cultured in Example 9.
Figure 16:
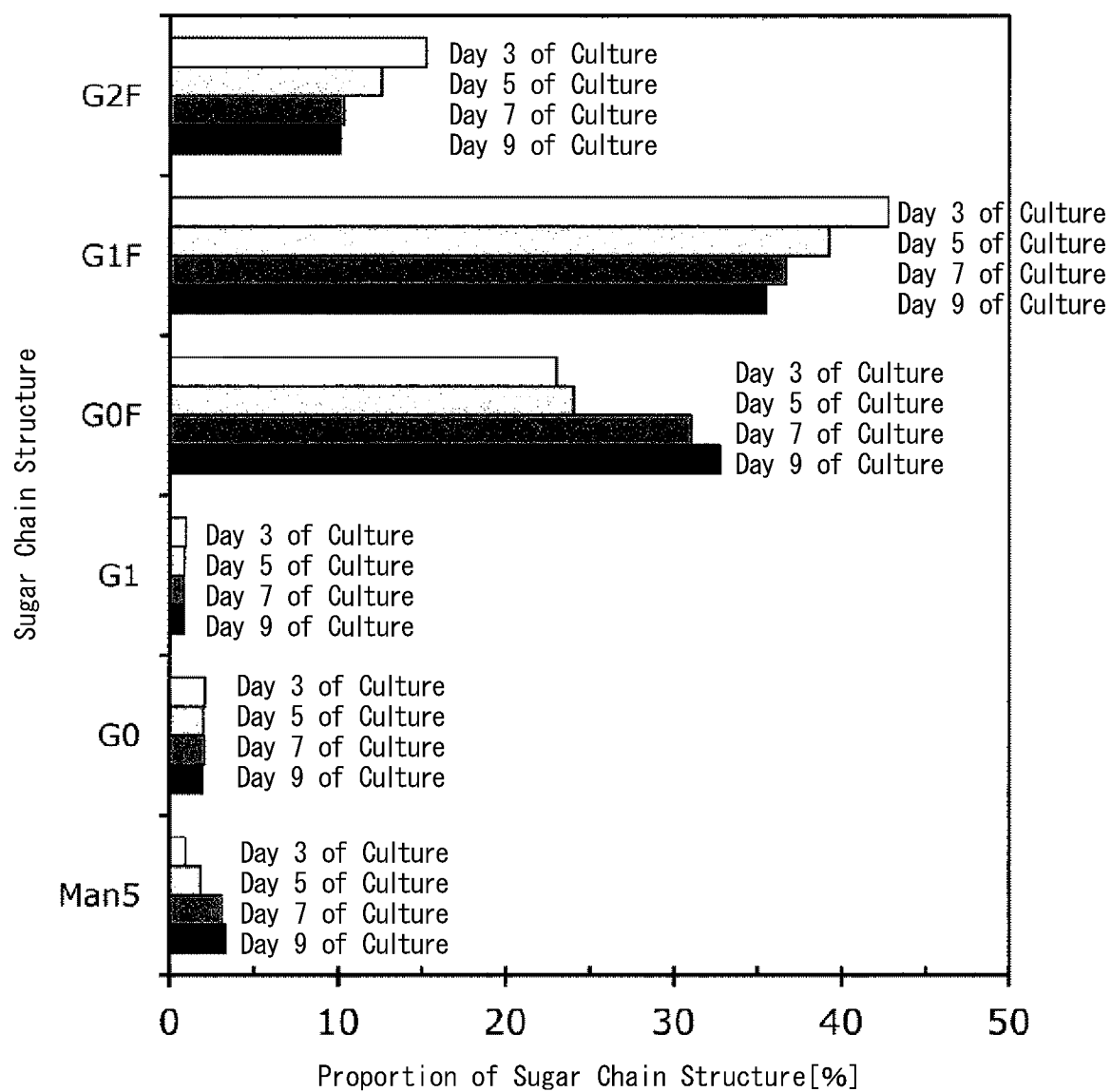
FIG. 16 is a graph indicating proportions of constituents in the sugar chain structure of the antibody obtained by the number of days of culture in Example 9.

Both FIG. 14 and Table 8 depict the summary results of the chromatogram (elution pattern) of each purified antibody obtained from the culture solution on a different day of culture and the area ratio of each peak calculated based on the chromatogram. In addition, FIG. 15 depicts the summary results of the viable cell concentration (viable cultured cell count) and the antibody concentration (antibody production) by the number of days of culture. Further, FIG. 16 and Table 9 depict the results of structural analysis of the sugar chain structure of the purified antibody. Others in Table 9 were specified as Man8, G0Fb–GN, G2, G1Fb–GN, G0Fa–GN, G1Fa–GN, G1F+SA, G2F+SA, G2F+SA2, and G1F+GN. Of these, G1F+SA was detected on Day 5 or later, and Man8 was detected on Day 7 or later.

From the results in FIG. 14 and Table 8, as in the case of the results obtained using the culture solution (Example 8 and FIG. 13), it was possible to recognize differences in the shape and height (peak area ratio) of a separation peak derived from the sugar chain structure of the antibody with the passage of days of culture. In addition, from the results in FIG. 16 and Table 9, it was confirmed that differences in the shape and height (peak area ratio) of a separation peak are based on differences in the sugar chain structure bound to the antibody. The above results indicate that by analyzing the culture solution during culture using the FcR9_F column of the present invention in a time-dependent manner, it is possible to conduct analysis in a step of culturing antibody-producing cells and monitor the sugar chain structure pattern of an antibody produced from the cells in a time dependent manner. Further, based on the results of monitoring the sugar chain structure pattern, it is possible to optimize culture conditions for obtaining an antibody having a desired sugar chain structure (capable of, for example, exhibiting performance as an antibody drug) and monitor culture steps.

TABLE 8

| | Peak No. | Elution time [min] | Number of days of culture | | | |
|---|---|---|---|---|---|---|
| | | | Day 3 | Day 5 | Day 7 | Day 9 |
| Area ratio [%] | Peak 1 | 9.6 | 18.1 | 22.3 | 33.8 | 34.4 |
| | Peak 2 | 11.7 | 36.7 | 38.1 | 35.6 | 35.4 |
| | Peak 3 | 13.7 | 45.2 | 39.6 | 30.6 | 30.2 |
| | Total | | 100 | 100 | 100 | 100 |

TABLE 9

| | Sugar chain structure | Number of days of culture | | | |
|---|---|---|---|---|---|
| | | Day 3 | Day 5 | Day 7 | Day 9 |
| Area ratio [%] | G2F | 15.24 | 12.58 | 10.35 | 10.14 |
| | G1F | 42.76 | 39.25 | 36.67 | 35.48 |
| | G0F | 23.03 | 24.06 | 31.06 | 32.76 |
| | G1 | 0.96 | 0.89 | 0.80 | 0.82 |
| | G0 | 2.11 | 2.00 | 2.07 | 1.95 |
| | Man5 | 0.92 | 1.83 | 3.10 | 3.33 |
| | others | 14.98 | 19.39 | 15.95 | 15.52 |
| | Total | 100 | 100 | 100 | 100 |

The present invention is described above in detail with reference to specific embodiments. However, it will be obvious to those skilled in the art that various changes and modifications can be made without departing from the spirit and scope of the present invention.

The entire contents of the specifications, sequence listings, claims, drawings, and abstracts of Japanese Patent Application No. 2017-028974 filed on Feb. 20, 2017, Japanese Patent Application No. 2017-074727 filed on Apr. 4, 2017, and Japanese Patent Application No. 2017-109681 filed on Jun. 2, 2017 are incorporated herein by reference and incorporated as the disclosure of the specification of the present invention.

The invention claimed is:

1. An Fc-binding protein comprising amino acid residues at positions 33 to 208 of the amino acid sequence set forth in SEQ ID NO: 9.

2. A method for separating an antibody, comprising:
adding an equilibration solution to a column which is filled with an insoluble carrier having the Fc-binding protein according to claim 1 immobilized thereon so as to equilibrate the column;
adding a solution containing an antibody to cause the antibody to be adsorbed on the carrier; and
eluting the antibody adsorbed on the carrier using an elution solution.

3. The separation method according to claim 2, further comprising isolating a fraction containing the eluted antibody.

4. The separation method according to claim 2, wherein the equilibration solution is a buffer containing an inorganic salt at pH 4.5 to pH 5.8.

5. A method for monitoring culture progress of an antibody-producing cell and/or a produced antibody, comprising:

obtaining an antibody-producing cell by transfecting a host cell with an antibody expression vector;
culturing the antibody-producing cell;
obtaining an antibody from the culture medium and/or cultured cells; and
separating the obtained antibody by the method according to claim 2.

6. A method for monitoring time-dependent changes in a sugar chain structure pattern of an antibody, comprising:
obtaining an antibody-producing cell by transfecting a host cell with an antibody expression vector;
culturing the antibody-producing cell;
obtaining an antibody from the culture medium and/or cultured cells; and
separating the obtained antibody by the method according to claim 2.

7. A method for producing an antibody, comprising optimizing culture conditions for an antibody-producing cell based on the results of monitoring by the method according to claim 6 such that the cell produces an antibody having a desired sugar chain structure.

* * * * *